(12) United States Patent
Terpetschnig et al.

(10) Patent No.: US 6,538,129 B1
(45) Date of Patent: Mar. 25, 2003

(54) LUMINESCENT COMPOUNDS

(75) Inventors: Ewald A. Terpetschnig, 12440 Alameda Trace Cir. 1936, Austin, TX (US) 78727; Leonid D. Patsenker, Kharkov (UA); Bernhard Oswald, Wenzenbach/Irlbach (DE)

(73) Assignee: Ewald A. Terpetschnig, Torrance, CA (US)

( * ) Notice: Subject to any disclaimer, the term of this patent is extended or adjusted under 35 U.S.C. 154(b) by 14 days.

(21) Appl. No.: 09/684,627

(22) Filed: Oct. 6, 2000

Related U.S. Application Data

(63) Continuation of application No. PCT/US99/07627, filed on Apr. 7, 1999.

(51) Int. Cl.[7] .......................... C07H 21/04; C12Q 1/68; C12Q 1/70
(52) U.S. Cl. .................. 536/26.6; 536/25.5; 435/6; 435/5
(58) Field of Search ....................... 435/6, 5; 536/26.6, 536/28, 28.5; 436/63, 94, 172; 546/176

(56) References Cited

U.S. PATENT DOCUMENTS

| | | |
|---|---|---|
| 3,996,345 A | 12/1976 | Ullman et al. |
| 3,998,943 A | 12/1976 | Ullman |
| 4,883,867 A | 11/1989 | Lee et al. |
| 5,101,015 A | 3/1992 | Brynes et al. |

FOREIGN PATENT DOCUMENTS

| | | | |
|---|---|---|---|
| WO | WO 97/40104 | * 10/1997 | ........... C09B/57/00 |

OTHER PUBLICATIONS

Oswald et al.("Synthesis, Spectral Properties, and Detection Limits of Reactive Squaraine Dyes, a New Class of Diode Laser Compatible Fluorescent Protein Labels", Bioconjugate Chem. vol. 10, pp. 925–931, 1999).*
Synthesis and Characterization of Unsymmetrical Squaraines: A New Class of Cyanine Dyes, Terpetschnig et al., *Dyes and Pigments*, vol. 21, pp. 227–234, 1993.
Synthesis, spectral properties and photostabilities of symmetrical and unsymmetrical squaraines; a new class of fluorophores with long–wavelength excitation and emission, Terpetschnig et al., *Analytica Chimica Acta*, vol. 282, pp. 633–641, 1993.
Synthesis of Squaraine–N–Hydroxysuccinimide Ester and Their Biological Application as Long–Wavelength Fluorescent Labels, Terpetsching et al., *Analytical Biochemistry*, vol. 217, pp. 197–204, 1994.

Synthesis, Spectral Properties, and Detection Limits of Reactive Squaraine Dyes, a New Class of Diode Laser Compatible Fluorescent Protein Labels, Oswald et al., *Bioconjugate Chem.*, vol. 10, pp. 925–931, 1999.

Red Laser–Induced Fluorescence Energy Transfer in an Immunosystem, Oswald et al., *Analytical Biochemistry*, vol. 280, pp. 272–277, 2000.

\* cited by examiner

*Primary Examiner*—Jeffrey Fredman
*Assistant Examiner*—Christine Maupin
(74) *Attorney, Agent, or Firm*—Kolisch Hartwell, P.C.

(57) ABSTRACT

Luminescent compounds, reactive intermediates used to synthesize luminescent compounds, and methods of synthesizing and using luminescent compounds. These compounds may be based on squaric, croconic, and rhodizonic acid, and their analogs, among others, and relate generally to the structure:

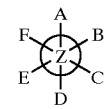

where Z is a four, five, or six-member aromatic ring, and A, B, C, D, E, and F are substituents of Z, in any order, that may include O, S, Se, Te, $C(R^a)(R^b)$, $N-R^c$, $N(R^d)(R^e)$, $W^1$, and $W^2$. Generally, each compound includes at least one of $W^1$ or $W^2$, where $W^1$ and $W^2$ have the structures:

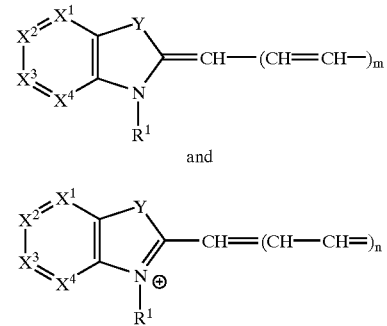

respectively. The compounds may include a reactive group and/or a carrier. The luminescent compounds may be useful in both free and conjugated forms as probes, labels, and/or indicators.

33 Claims, 1 Drawing Sheet

LUMINESCENT COMPOUNDS

CROSS-REFERENCES TO RELATED APPLICATIONS

This application is a continuation of PCT Patent Application Ser. No. PCT/US99/07627, filed Apr. 7, 1999, which is incorporated herein by reference.

This application is based upon and claims benefit under 35 U.S.C. §119 and other applicable national and international law of the following patent applications, each of which is incorporated herein by reference: Deutsches Patentamt Application Serial No. 198 15 659.6, filed Apr. 8, 1998 in the German Patent Office, entitled REAKTIVE QUADRATSÄURE- UND CROCONSÄURE-FARBSTOFFE ALS MARKER FÜR BIOMOLEKÜLE UND ARZNEISTOFFE, and naming Ewald Terpetschnig as inventor; and U.S. Provisional Patent Application Serial No. 60/083,820, filed May 1, 1998.

This application incorporates by reference the following publications: Joseph R. Lakowicz, Principles of Fluorescence Spectroscopy (1983); Richard J. Lewis, Sr., Hawley's Condensed Chemical Dictionary (12$^{th}$ ed. 1993).

FIELD OF THE INVENTION

The invention relates to luminescent compounds, and more particularly to luminescent compounds based on squaric, croconic, or rhodizonic acid, among others.

BACKGROUND OF THE INVENTION

A luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. A luminescence lifetime is the average time that a luminophore spends in the excited state prior to returning to the ground state. A quantum yield is the ratio of the number of photons emitted to the number of photons absorbed by a luminophore.

Luminescence methods may be influenced by extinction coefficient, excitation and emission spectra, Stokes' shift, and quantum yield, among others, and may involve characterizing fluorescence intensity, fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Luminescence methods have several significant potential strengths. First, luminescence methods may be very sensitive, because modern detectors, such as photomultiplier tubes (PMTs) and charge-coupled devices (CCDs), can detect very low levels of light. Second, luminescence methods may be very selective, because the luminescence signal may come almost exclusively from the luminophore.

Despite these potential strengths, luminescence methods suffer from a number of shortcomings, at least some of which relate to the luminophore. For example, the luminophore may have an extinction coefficient and/or quantum yield that is too low to permit detection of an adequate amount of light. The luminophore also may have a Stokes' shift that is too small to permit detection of emission light without significant detection of excitation light. The luminophore also may have an excitation spectrum that does not permit it to be excited by wavelength-limited light sources, such as common lasers and arc lamps. The luminophore also may be unstable, so that it is readily bleached and rendered nonluminescent. The luminophore also may have an excitation and/or emission spectrum that overlaps with the well-known autoluminescence of biological and other samples; such autoluminescence is particularly significant at wavelengths below about 600 nm. The luminophore also may be expensive, especially if it is difficult to manufacture.

SUMMARY OF THE INVENTION

The invention provides photoluminescent compounds, reactive intermediates used to synthesize photoluminescent compounds, and methods of synthesizing and using photoluminescent compounds, among others. X The compounds relate generally to the following structure:

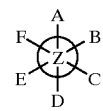

Here, Z is a four, five, or six-member aromatic ring, and A, B, C, D, E, and F are substituents of Z, where F is absent when Z is a five-member ring, and where E and F are absent when Z is a four-member ring. Generally, A, B, C, D, E, and F may be present in any order, although the order may be limited in certain embodiments.

A, B, C, D, E, and F are selected from a variety of elements and groups, including but not necessarily limited to O, S, Se, Te, C(R$^a$)(R$^b$), N—R$^c$, N(R$^d$)(R$^e$), W$^1$, and W$^2$.

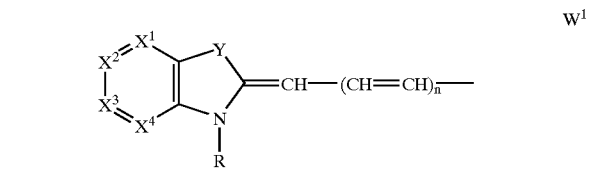

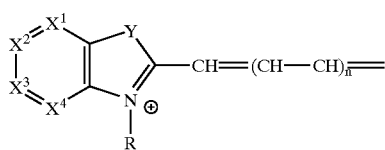

The components $R^a$, $R^b$, $R^c$, $R^d$, $R^e$, n, $X^1$, $X^2$, $X^3$, $X^4$, and Y are defined in detail in the Detailed Description. However, generally, each compound includes at least one of $W^1$ or $W^2$, with the preferred synthetic precursors including one, and the preferred photoluminescent compounds including two. In some embodiments, the compound includes at least one S. In other embodiments, the compound includes at least one heteroatom in $X^1$ through $X^4$ of $W^1$ or $W^2$. In yet other embodiments, the compound includes a reactive group and/or a carrier. In yet other embodiments, A, B, C, D, E, and F are chosen so that the compound is photoluminescent.

The methods relate generally to the synthesis and/or use of photoluminescent compounds, especially those described above.

The nature of the invention will be understood more readily after consideration of the drawing, chemical structures, and detailed description of the invention that follow.

ABBREVIATIONS

Figure 1:
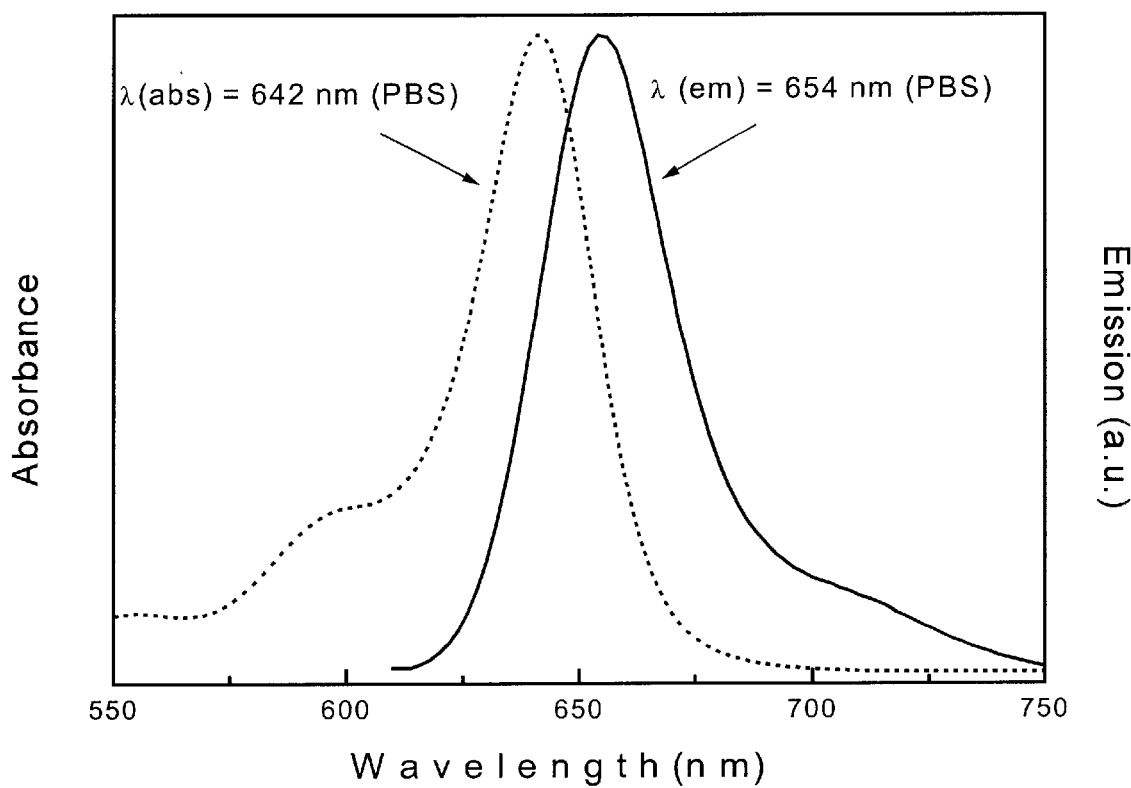
FIG. 1 is a graph showing excitation (dotted line) and emission (solid line) spectra for (13)-HSA in phosphate-buffered saline (PBS).

The following abbreviations, among others, may be used in this application:

| | |
|---|---|
| BSA | bovine serum albumin |
| Bu | butyl |
| DCC | dicyclohexylcarbodiimide |
| DMF | dimethylformamide |
| D/P | dye-to-protein ratio |
| Et | ethyl |
| g | grams |
| h | hours |
| HSA | human serum albumin |
| hCG | human chorionic gonadotropin |
| L | liters |
| m | milli ($10^{-3}$) |
| M | molar |
| Me | methyl |
| mol | moles |
| M.P. | melting point |
| n | nano ($10^{-9}$) |
| NHS | N-hydroxysuccinimide |
| NIR | near infrared region |
| PBS | phosphate-buffer saline |
| Prop | propyl |
| TMS | tetramethylsilane |
| TSTU | N,N,N',N'-tetramethyl(succinimido)uronium tetrafluoroborate |
| $\mu$ | micro ($10^{-6}$) |

DETAILED DESCRIPTION OF THE INVENTION

The invention relates generally to photoluminescent compounds and their synthetic precursors, and to methods of synthesizing and using such compounds. These photoluminescent compounds may be useful in both free and conjugated forms, as probes, labels, and/or indicators. This usefulness may reflect in part enhancement of one or more of the following: quantum yield, Stokes' shift, extinction coefficients, and photostability. This usefulness also may reflect excitation and emission spectra in relatively inaccessible regions of the spectrum, including the red and near infrared.

The remaining discussion includes (1) an overview of structures, (2) an overview of synthetic methods, and (3) a series of illustrative examples.

Overview of Structures

The photoluminescent compounds and their synthetic precursors generally comprise the following structure:

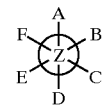

Here, Z is a four, five, or six-member aromatic ring, and A, B, C, D, E, and F are substituents of Z, where F is absent if Z is a five-member ring, and where E and F are absent if Z is a six-member ring. A, B, C, D, E, and F may be singly or doubly bonded to Z.

Ring Z may take a variety of forms. Preferred rings are based on four-member squaric acid, five-member croconic acid, and six-member rhodizonic acid, and/or their analogs, with substitutions as described below.

Substituents A, B, C, D, E, and F also may take a variety of forms. Preferred substituents include O, S, Se, Te, $C(R^a)$ $(R^b)$, N—$R^c$, $N(R^d)(R^e)$, $W^1$, and $W^2$. $R^a$, $R^b$, and $R^c$ may be selected from the group consisting of aliphatic, heteroatom-substituted aliphatic, polyether, aromatic, reactive aliphatic, and reactive aromatic groups, among others. $R^d$ and $R^e$ may be selected from the group consisting of carboxylic acid, cyano, carboxamide, carboxylic ester, and aliphatic amine groups, among others.

$W^1$ and $W^2$ may include the following structures, among others:

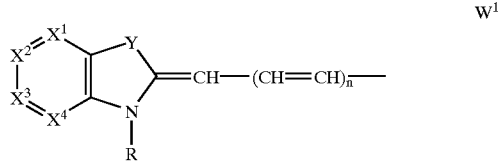

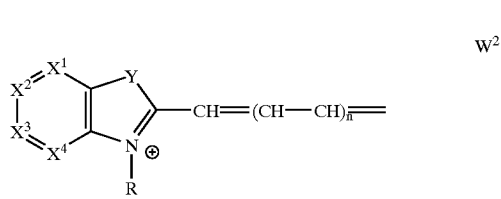

For each of $W^1$ and $W^2$, the variables n, Y, R, and $X^1$ through $X^4$ generally may be defined independently, as follows. n may be 0, 1, or 2. Y may be O, S, Se, Te, N—$R^f$, and $C(R^g)(R^h)$. $R^f$ may be H, aliphatic groups, alicyclic groups, aromatic groups, and reactive aliphatic groups, among others. $R^g$ and $R^h$ may be aliphatic and reactive aliphatic groups, among others. R may be H, aliphatic groups, alicyclic groups, aromatic groups, linked carriers, :reactive groups capable of covalent attachment to a carrier, spacers bound to one or more reactive groups capable of covalent attachment to a carrier, and ionic substituents capable of increasing the hydrophilicity of the entire compound, among others. Finally, $X^1$, $X^2$, $X^3$, and $X^4$ may be N, O, S, and C—$R^i$. $R^i$ may be H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring, among others. The substituents on the substituted rings may be chosen quite broadly, and may include the various component listed above, among others. If any of $X^1$–$X^4$ includes a part of an unsubstituted or substituted ring, then any of $X^1$–$X^4$ may optionally form a ring with any other of $X^1$–$X^4$, particularly an adjacent other. Such rings may be independently selected from the group of ring systems consisting of cyclic alkyl, substituted cyclic alkyl, aryl, substituted aryl, heteroaryl, substituted heteroaryl, heterocyclyl, and heterocyclyl ring systems, among others.

Finally, any or all of the hydrogens (H) in the compound may be independently replaced by fluorines (F), which may improve the photostability and/or quantum yield of the compound.

Photoluminescent compounds. In the photoluminescent compounds, B and C are typically chosen from $W^1$ and/or $W^2$, and A, B, C, D, E, and F typically are present in any order. If B and C are adjacent, then each of B and C is $W^1$, and each of A, D, E, and F is neutral. If B and C are separated by one of A, D, E, or F, then one of B and C is $W^1$, one of B and C is $W^2$, and one of A, D, E, and F is negatively charged. If B and C are separated by two of A, D, E, and F, which is possible only in the six-member ring, then each of B and C is $W^2$, and each of A, D, E, and F is neutral.

Representative structures for the photoluminescent compounds are shown below, where $W^1$ and $W^2$ represent the structures defined above, and where $V^1$ through $V^4$ represent the structures A, D, E, and F as defined above, in any order.

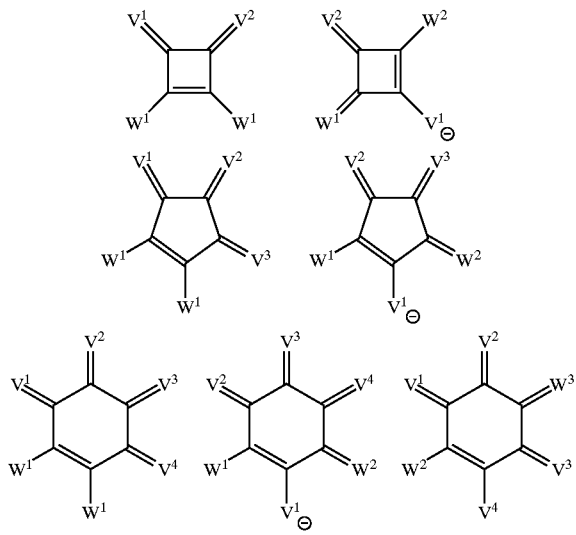

Depending on the embodiment, A, B, C, D, E, and F may be subject to additional limitations. In some embodiments, the compound also includes at least one of S, Se, Te, and C($R^a$)($R^b$). In other embodiments, the compound also includes at least one heteroatom in $X^1$ through $X^4$ of $W^1$ or $W^2$. In yet other embodiments, the compound also includes a reactive group and/or a carrier.

Synthetic precursors. In the synthetic precursors, B typically is one of $W^1$ and $W^2$, and C is analogous to D, E, and F. A representative precursor in which Z is a four-member ring is shown below.

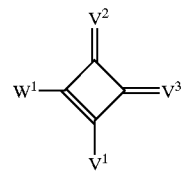

Here, $V^1$ may be $O^-$, $S^-$, OH, SH, OR (Me, Et, i-Prop, Butyl, etc.), SR, NRH, NRR; and $[C(R)(R)]^-$, among others, where R may be CN, COOH, C(=O)NHR, COOEt, COOCH$_3$, among others. $V^2$ and $V^3$ may be O, S, NR, and CRR, among others, where R may be CN, COOH, C(=O)NHR, and COOEt, among others.

Analogous precursors in which Z is a five or six-member ring also may be used.

Tandems. Luminescent compounds in accordance with the invention also may involve pairs, triplets, and higher numbers of compounds conjugated together to form a single compound. Such "tandems" may be used to obtain alternative spectral properties, such as enhanced Stokes' shifts. Such tandems also may be used in energy transfer. Such tandems also may be used for other purposes. Some potential combinations are drawn below, where A, B, C, D, E, F, and Z have their usual meanings, and U represents a cross-link, such as formed by a reactive compound. Z and each substituent may be chosen independently for each component of a tandem.

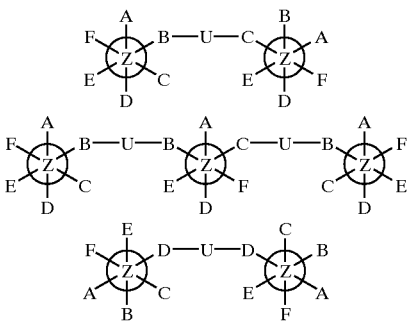

Carrier groups. The photoluminescent compound and/or its synthetic precursors may be covalently or noncovalently associated with one or more carrier groups. Covalent association may occur through various mechanisms, including a reactive group, and may involve a spacer for separating the photoluminescent compound or precursor from the carrier. Noncovalent association also may occur through various mechanisms, including incorporation of the photoluminescent compound or precursor into or onto a matrix, such as a bead or surface, or by nonspecific interactions, such as hydrogen bonding, ionic bonding, or hydrophobic interactions. Carriers may include any suitable reaction or binding partner, among others, including polypeptides, polynucleotides, beads, microplate well surfaces, and other solid surfaces.

Reactive groups. The substituents of Z may include one or more reactive groups, where a reactive group generally is a group capable of forming a covalent attachment with another molecule or substrate. Such other molecules or substrates may include proteins, carbohydrates, nucleic acids, and plastics, among others. Reactive groups vary in their specificity, preferentially reacting with particular functionalities. Thus, reactive compounds generally include reactive groups chosen preferentially to react with functionalities found on the molecule or substrate with which the reactive compound is intended to react.

The following reactive groups, among others, may be used in conjunction with the photoluminescent compounds and reactive intermediates described here:

a) N-hydroxysuccinimide esters, isothiocyanates, and sulfonylchlorides, which form stable covalent bonds with amines, including amines in proteins and amine-modified nucleic acids b) Iodoacetamides and maleimides, which form covalent bonds with thiol-functions, as in proteins c) Carboxyl functions and various derivatives, including N-hydroxybenztriazole esters, thioesters, p-nitrophenyl esters, alkyl, alkenyl, alkynyl, and aromatic esters, and acyl imidazoles.

d) Alkylhalides, including iodoacetamides and chloroacetamides e) Hydroxyl groups, which can be converted into esters, ethers, and aldehydes f) Aldehydes and ketones and various derivatives, including hydrazones, oximes, and semicarbozones g) Isocyanates, which react with amines h) Activated C=C double-bond-containing groups, which can react in a Diels-Alder reaction to form stable ring systems under mild conditions i) Thiol groups, which can form disulfide bonds and react with alkylhalides (iodoacetamide)

j) Alkenes, which can undergo a Michael addition with thiols, e.g., maleimide reactions with thiols k) Phosphoramidites, which can be used for direct labeling of nucleosides, nucleotides, and oligonucleotides, including primers on a solid support R groups. The R groups associated with the various substituents of Z may include any of a number of groups, as described above, including but not limited to alicyclic groups, aliphatic groups, aromatic groups, and heterocyclic rings, as well as substituted versions thereof.

Alicyclic groups include groups of organic compounds characterized by arrangement of the carbon atoms in closed ring structures sometimes resembling boats, chairs, or even bird cages. These compounds have properties resembling those of aliphatics and should not be confused with aromatic compounds having the hexagonal benzene ring. Alicyclics comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aliphatic groups include groups of organic compounds characterized by straight-or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked.

Aromatic groups include groups of unsaturated cyclic hydrocarbons containing one or more rings. A typical aromatic group is benzene, which has a 6-carbon ring containing three double bonds. Most aromatics are highly reactive and chemically versatile. Most aromatics are derived from petroleum and coal tar. Some 5-membered cyclic compounds, such as the furan group (heterocyclic), are analogous to aromatic compounds.

Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine.

Overview of Synthesis and Characterization

The synthesis of photoluminescent compounds according to the invention typically is achieved in a multi-step reaction, starting with the synthesis of a methylene base. The synthesis of suitable bases may proceed based on literature or novel methods. Generally, the spectral properties of the photoluminescent compounds, including excitation and emission wavelength, are strongly dependent on the type of methylene base used. Typical starting materials include benzindoles, benzoselenzoles, benzoxazoles, benzimidazoles, etc., and squaric acid. Squaric acid is a dibasic acid that undergoes a series of nucleophilic substitution reactions with various reagents, including amines, phenols, and CH-acidic compounds such as 1,2,3,3-tetramethl-benzindole. The squaraine bridge in the resulting compounds stabilizes the conjugated chain and shifts the excitation and emission wavelength of these dyes to the red as compared to cyanine-based dyes. In particular, the exchange of the oxygen in the squaraine moiety by sulfur or a methylene ($=CR_2$)— functionality is shown here to be a pathway to a new group squaraine dyes with useful fluorescence properties.

In the examples that follow this section, the synthesis and spectral characterization of several long-wavelength fluorescent labels based on squaraine and other dyes is presented, including some reactive versions. These dyes may include a cyanine-type chromophore and a squarate bridge. To achieve water-solubility, sulfonic acid or other groups may be introduced into the heterocyclic ring systems, and to permit covalent attachment to proteins, reactive N-hydroxy-succinimide ester (NHS ester) or other forms may be synthesized. To modify the spectral properties of the dyes, sulfo- and dicyanomethylen-substituted versions of the squaraines were synthesized and tested for their potential use for labeling of biopolymers. The squaraine-based markers exhibit lower quantum yields in water ($\phi=0.15$) and very high quantum yields ($\phi=0.5–0.7$) when bound to biomolecules. The absorption and emission wavelengths can be tuned by substitution of the squaraine ring or by introducing heteroatoms into the heterocyclic moiety. Thus, the indolenine-squaraines and thiosquaraines absorb around 635 to 640 in water and at approximately 645 to 650 nm when bound to proteins. The absorption and emission spectra of benzothiazolium and benzoselenzolium squaraines on the other hand are shifted towards longer wavelengths. Typical emission wavelengths for such squaraine dyes are around 680 nm to 690 nm for benzothiazole dyes and beyond 700 nm for benzoselenzole derivatives. Importantly, the Stokes' shift increases in these longer wavelength-emitting dyes, which ultimately increases the sensitivity of a fluorescent measurement.

The resulting dyes show absorption and emission maxima beyond 600 nm and their wavelength can be tuned by changing the heterocyclic moiety and/or the substitution on the squaraine ring system. The Stokes' shift of the sulfur or methylene derivatives of symmetric squaraines (9), (13), and

(15) is increased more than 2.5 times relative to the Stokes' shift of the analogous oxygen-containing squaraines (8) and (3b). In addition, the replacement of C=O by C=C or C=S in example (15) or example (9) results in a bathochromic shift of both, the absorption and the emission properties of these dyes. A further increase of the Stokes' shift can be achieved by introducing asymmetry into the molecule. Thus, the asymmetric versions (13) and (15) are expected to have even higher Stokes' shifts.

Various methods may be used for synthesizing dithiosquaraine dyes.

In one approach, dithio-squaraine dyes are synthesized from their oxygen analogs, using $P_2S_{10}$ as a reagent.

In another approach, described in Example 5, a dithiosquaraine dye is synthesized using a 1,3,3-trimethyl-2-indolinylidene methyl-substituted squaraine that is allowed to react with $P_4S_{10}$. The dithiosquaraine could be synthesized in sufficient yield using 1.2 equivalents of $P_4S_{10}$. Elemental analysis and absorption and emission spectral data were used to characterize the reaction product, which showed bright emission with a Stokes' shift of 49 nm in chloroform.

In yet another approach, an asymmetric squaraine dye was synthesized and reacted with $P_4S_{10}$ using pyridine as solvent. After reacting the squaraine compound with $P_4S_{10}$, a new long-wavelength emitting compound was isolated. The absorption and emission spectral properties were clearly distinguishable from those of the parent oxo derivative. The exchange of oxygen for sulfur in dye (11) led to a 14-nm increase of the Stokes' shift, resulting in a total shift of 37 nm. An increased Stokes' shift results in improved sensitivity for fluorescence measurements, due to better separation of the excitation and emission maxima, allowing the molecules to be excited at their absorbance maximum, rather than at shorter wavelengths with lower extinction coefficients.

All attempts to synthesize the thio-analogues of sulfonato-squaraine derivatives using $P_4S_{10}$ or Lawessons Reagent failed. A number of deep blue colored products were obtained, but their purification appeared to be very difficult. The route using dithiosquaric acid disodium salt as a starting material appeared to be more successful. This starting material was synthesized in a two-step reaction from squaric acid using DMF and aminophenol and subsequently sodium hydrogen sulfide as reagents. Using dithiosquaric acid as starting material, the dithio-analogue of the symmetric squaraine dye (13) was synthesized and characterized using $^1$H-NMR, absorption and emission spectral data. The reaction controlled by TLC clearly shows two products with different $R_f$ values: $R_f$: 0.75 for the diacid (13) and a minor spot with an $R_f$: 0.55 presumably for the dibutylester which is due to the esterification of the $\epsilon$-carboxylic acid functions in BuOH. In contrast to the thiosquaric acid, the dibutylester formation is preferred in the dioxo-squaraine synthesis pathway, and thus the ester is the main product. The spectral properties of the thiosquaraine dye remain very similar to its dioxo-analogue, except for the lower extinction coefficient and the bigger Stokes' shift of the dithio-dye. For covalent attachment to proteins the NHS-ester was synthesized, and labeling to a protein was demonstrated using HSA. Importantly, the quantum yields of the dithiosquaraine dyes also increase on covalent binding to proteins. Thus, the quantum yield of the HSA-conjugates were also found to be around 60–70%, which makes them comparable to those of their dioxo derivatives. The quantum yields were determined using Cy 5™ as a reference.

The substitution of one oxygen or sulfur of the central squarate bridge with CH-acidic reagents e.g. dicyanomethane, HOOC—($CH_2$)—COOH, or ROOC—($CH_2$)—CN leads to the group of luminescent methylenesquaraine derivatives. As compared to the basic squaraines these compounds have red-shifted excitation and emission properties and larger Stokes' shifts. The absorption and emission maxima of a representative reactive dye (15) (example 7) were found to be 667 nm and 685 nm in PBS, respectively.

Example 8 demonstrates the conversion of a croconium dye into a reactive protein label. Croconium dyes are cyanine dyes which contain a five-member central croconium bridge. As compared to cyanine dyes the croconium bridge shifts the excitation and emission wavelength of these dyes about 100 nm to the red and improves their photostability. The excitation and emission wavelengths of a substituted benzothiazolium croconium dyes in methanol was measured be 750 nm and 788 nm, respectively. The conversion of a sulfonated croconium dye into a reactive sulfonyl chloride was achieved by reaction of the dye with $PCl_5$ and subsequent extraction of the reactive dye into $CHCl_3$.

Example 9 describes synthetic pathways to unsymmetrical thiosquaraine and methylenesquaraine dyes. The key intermediates for this subgroup of squaraine dyes are mono-substituted thiosquaraine and methylenesquaraine derivatives, which are synthesized by reacting the 1,3-dithiosquaric acid disodium salt (2c) or 4-dicyanomethylene-2,3-dibutyl squarate (2d) with 1 equivalent of indolenine (1a). Subsequently the intermediate is reacted with one equivalent of a different methylene base. The synthesis of unsymmetrical squaraine dyes allows access to mono-functional reactive squaraine dyes (Scheme 1). Such dyes show improved labelling performance because of reduced crosslinking with proteins.

Example 10 shows structures of thiosquaraine and methylenesquaraine based dyes that should further demonstrate the variety of structures that can be synthesized from this invention. Most of the representative structures are based on reactive water-soluble dyes showing different substitution patterns on the central bridge. Two of the structures contain phosphoramidite linkages for direct coupling used in solid support DNA or RNA synthesis. Sulfonated and non-sulfonated versions of squaraine dyes can be used for the synthesis of phosphoramidites. The phosphoramidite linkage can either be incorporated in the heterocyclic bases or can be attached to the central squarate ring via activation of a carboxyl-cyano methylene function to an NHS ester and reacting it with an amino-alcohol spacer group. The introduced hydroxyl function is then converted by standard procedures into a phosphoramidite. Fluorinated versions of the invention as exemplified in Example 10 may exhibit improved photostability and higher quantum yields. Fluorine atoms can be introduced in the heterocyclic bases and/or in the bridge.

EXAMPLE 1

Synthesis of Precursors

This section describes the synthesis of various precursors. p-hydrazinobenzenesulfonic acid (Illy et al., J. Org. Chem. 33, 4283–4285 (1968)), 1-($\epsilon$-carboxypentyl)-2,3,3-trimethylindolenium-5-sulfonic acid potassium salt (1a), 2,3,3-trimethylindole-5-sulfonic acid potassium salt (Mujumdar et al., Bioconj. Chem. 4, 105–111 (1993)) (1b), and 1,2,3,3-tetramethylindoleninium-5-sulfonate (1c) were synthesized using literature procedures. 1,3-dithiosquaric acid disodium salt (2c) and dicyanomethylene-dimethylsquarate (2d) were synthesized according to G.

Seitz et al., Chem. Ber. 112, 990–999 (1979), and B. Gerecht et al., Chem. Ber. 117, 2714–2729 (1984), respectively.

Preparation of 1-(ε-carboxypentyl)-2,3,3-trimethylindolenium-5-sulfonic acid potassium salt (1a)

p-Hydrazinobenzenesulfonic acid 33 g of sodium carbonate was added to a suspension of 104 g (0.6 mol) of p-aminobenzenesulfonic acid in 400 mL of hot water. The solution was cooled to 5° C. in an ice-bath, and 70 g of concentrated sulfuric acid were added slowly under rapid stirring. A solution of 42 g of sodium nitrite in 100 mL of water was then added under cooling. A light yellow diazo-compound precipitate formed, which was filtered and ashed with water, but not dried.

The wet diazo-compound was added under stirring and cooling (5° C.) to a solution of 170 g of sodium sulfite in 500 mL of water. The solution, which turned orange, was stirred under cooling for 1 h, and then heated to reflux. Finally, 400 mL of concentrated hydrochloric acid were added. The solution turned yellow, and the product precipitated as a white solid. For complete decoloration, 1–2 g of powdered zinc were added. The reaction mixture was cooled overnight, and the precipitate was filtered, washed with water, and dried in an oven at 100° C.

Yield: 96 g (85%), white powder; M.P.=286° C. (Lit.= 285° C.); $R_f$: 0.95 (RP-18, water:MeOH 2:1).

Preparation of 2,3,3-trimethylindole-5-sulfonic acid, potassium salt (1b)

18.2 g (0.12 mol) of p-hydrazinobenzenesulfonic acid and 14.8 g (0.17 mol) of isopropylmethylketone were stirred in 100 mL of glacial acetic acid at room temperature for 1 h. The mixture was then refluxed for 4 h. The mixture was cooled to room temperature, and the resulting pink solid precipitate was filtered and washed with ether.

The precipitate was dissolved in methanol, and a concentrated solution of potassium hydroxide in 2-propanol was added until a yellow solid completely precipitated. The precipitate was filtered, washed with ether, and dried in a desiccator over $P_2O_5$.

Yield: 20.4 g (71%), off-white powder; M.P.=275° C.; $R_f$: 0.40 (silica gel, isopropanol:water:ammonia 9:0.5:1).

1(ε-carboxypentyl)-2,3,3-trimethylindolenium-5-sulfonic acid, potassium salt (1a)

15.9 g (57 mmol) of 2,3,3-trimethylindolenium-5-sulfonic acid potassium salt and 12.9 g (66 mmol) of 6-bromohexanoic acid were refluxed in 100 mL of 1,2-dichlorobenzene for 12 h under a nitrogen atmosphere. The solution was cooled to room temperature, and the resulting pink precipitate was filtered, washed with chloroform, and dried.

Yield: 15.8 g (58%), pink powder; $R_f$: 0.75 (RP-18, MeOH:water 2:1).

Synthesis of 1,2,3,3-tetramethylindoleninium-5-sulfonate (1c)

1.1 g of 2,3,3-trimethylindolenium-5-sulfonate were suspended in 30 mL of methyl iodide. The reaction mixture was heated to boiling for 25 h in a sealed tube. After the mixture was cooled, excess methyl iodide was decanted, and the residue was suspended in 50 mL of acetone. The solution was filtered, and the residue was dried in a desiccator over $CaCl_2$. The resulting light yellow powder was used without further purification.

Yield: 90%, light yellow powder.

| 1 | $R_1$ | $R_2$ | $A^-$ |
|---|---|---|---|
| a | $(CH_2)_5COOH$ | $SO_3K$ | I |
| b | — | — | — |
| c | $CH_3$ | $SO_3K$ | I |

| 2 | $R_1$ | $R_2$ | $R_3$ | $R_4$ |
|---|---|---|---|---|
| a | O | O | OH | OH |
| b | O | O | $OC_4H_9$ | $OC_4H_9$ |
| c | S | O | $S^-Na^+$ | $O^-Na^+$ |
| d | O | $CH_2(CN)_2$ | $OCH_3$ | $OCH_3$ |

EXAMPLE 2

Synthesis of 2,4-bis[N-(carboxypentyl)-3,3-dimethyl-5-sulfo-2-indolinylidene methyl] cyclobutenediylium-1,3-diolate (3b)

Synthesis of the di-butylester (3a)

120 mg (1.03 mmol) of squaric acid (2a) were added to 1 g (2.17 mmol) of 1-(ε-carboxypentyl)-2,3,3-trimethylindolenium-5-sulfonic acid potassium salt (1a). The resulting mixture was refluxed in 50 mL of 1-butanol:toluene (1:1, v:v) for 22 h using a Dean-Stark trap filled with 4A molecular sieve. After the mixture was cooled, the solvent was removed, and the product was purified by preparative thin-layer chromatography using RP-18 glass plates and methanol:water (2:1, v:v) as eluent to give 3a.

Yield: 90 mg (22%) of 3a; M.P.>300° C.; $R_f$: 0.47 (RP-C18, methanol/water 2/1); FAB-MS, m/e ($M^+$, dianion) for $C_{46}H_{58}N_2O_{12}S_2K_2$, calculated 895.1, found 894.8; $^1H$-NMR ($D_2O$): δ7.7–7.1 (m, 6H), 5.7 (s, 2H), 3.7 (t, 4H, J=6.5), 2.0 (t, 4H, J=7 Hz), 1.55–0.9 (m, 24H), 1.45 (s, 12H), 0.5 (t, 6H, J=7 Hz; $\lambda_{max}$ (abs)=634 nm (PBS), $\lambda_{max}$ (em)= 642 nm (PBS).

Synthesis of di-acid (3b)

1 mL of water and 20 mL of 1 M HCl were added to 50 mg (0.05 mmol) of Sq635-b-butylester (3a). The resulting mixture was heated to 100° C. for 80 min At the end of the reaction, 5 mL of 1 M HCl were added. After the mixture was cooled, the solvent was removed, and the product was vacuum dried. The product was used without further purification.

Yield: 43 mg (99%); M.P.>300° C.; $R_f$: 0.75 (RP-C18, methanol:water 2:1); FAB-MS, m/e ($M^+$, dianion) for $C_{38}H_{42}N_2O_{12}S_2K_2$, calculated 782.9, found 783.0; $^1H$-NMR ($D_2O$); δ7.8–7.3 (m, 6H), 5.9 (s, 2H), 4.2 (t, 4H, J=6.5 Hz), 2.4 (t, 4H, J=7 Hz), 1.95–1.3 (m, 12H), 1.77 (s, 12H); $\lambda_{max}$(abs)=635 nm (PBS); $\lambda_{max}$(em)=642 nm (PBS).

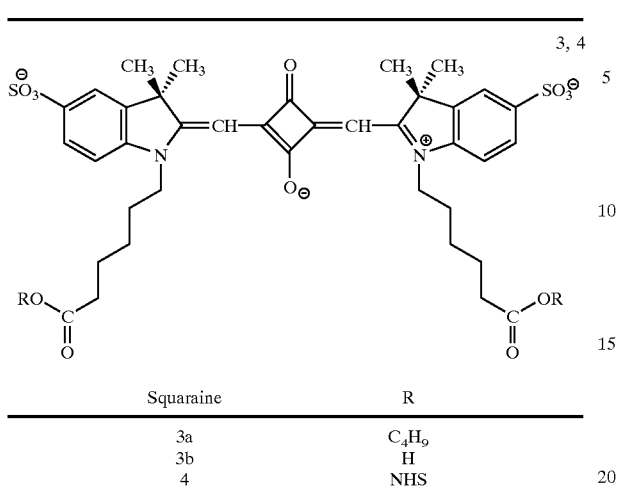

| Squaraine | R |
|---|---|
| 3a | C₄H₉ |
| 3b | H |
| 4 | NHS |

Synthesis of bis-NHS-ester (4)

a) With TSTU (N,N,N',N'-tetramethyl(succinimido)uronium tetrafluoroborate)

26 μl (0.15 mmol) of diisopropylethylamine and 38 mg (0.126 mmol) of TSTU were added to a mixture of 43 mg (0.05 mmol) of Sq635-b-acid (3b) in 1 mL of DMF, 1 mL of dioxane, and 0.5 mL of water. After 30 min, the mixture was filtered, and the solvents were removed in vacuum. The product was dried over $P_2O_5$ and used without further purification.

Yield: 40 mg (76%); M.P.>300° C.; $R_f$: 0.82 (RP-C18, methanol:water 2:1); FAB-MS, m/e ($M^+$, dianion) for $C_{46}H_{48}N_4O_{16}S_2K_2$, calculated 977.0, found 977.1; ε=140,000 L/(mol*cm).

b) With NHS/DCC 1 mL of anhydrous DMF was added to a mixture of 20 mg (0.023 mmol) of Sq635-b-acid (3b), 14 mg (0.069 mmol) of dicyclohexylcarbodiimide (DCC), and 8 mg (0.069 mmol) of N-hydroxysuccinimide (NHS). The solution was stirred for 24 h at room temperature and then filtered. The solvent was removed in vacuum, and the product was triturated with ether and dried over $P_2O_5$.

Yield: 22 mg (91%); M.P.>300° C.; $R_f$: 0.82 (RP-C18, methanol:water 2:1); FAB-MS, m/e ($M^+$, dianion) for $C_{46}H_{48}N_4O_{16}S_2K_2$, calculated 977.0, found 977.2.

EXAMPLE 3

Synthesis of 2-[N-(5-carboxypentyl)-3,3-dimethyl-5-sulfo-2-indolinylidene methyl]-4-[3,3-dimethyl-5-sulfo-2-indolinylidenemethyl]cyclobutenediylium-1,3-diolate (6a)

Synthesis of mono-acid (6a)

22 μl (0.1 mmol) of squaric acid dibutyl ester were added to 47 mg (0.1 mmol) of 1-(ε-carboxypentyl)-2,3,3-trimethylindolenium-5-sulfonic acid potassium salt (1a). The resulting mixture was refluxed in 8 mL of ethanol with 140 μL of triethylamine for 30 min. 220 μl of 1 M aqueous NaOH were then added, and the mixture was refluxed for 30 min. After the mixture was cooled to room temperature, 2.3 mL of 1 M hydrochloric acid were added, and the solvent was removed under reduced pressure to obtain the mono-substituted squaraine derivative (5a).

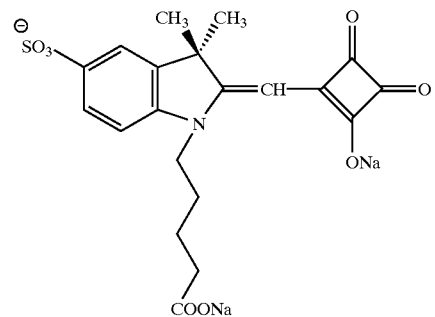

The residue was refluxed with 24 mg (0.09 mmol) of 2,3,3-trimethylindole-5-sulfonic acid (1b) potassium salt in butanol:toluene (1:1 v:v) for 1 h. Water was removed as an azeotrope using a Dean-Stark trap. After cooling, the solvents were removed using a rotary evaporator. The product was treated with 100 μL of methanol, collected under reduced pressure, and purified on preparative TLC (RP-18 $F_{254S}$) using methanol:water (2:1 v:v) as the eluent.

Yield: 31 mg (33%); M.P.>300° C.; $R_f$: 0.50 (RP-C18, methanol:water 2:1); FAB-MS, m/e ($M^+$, dianion) for $C_{32}H_{32}N_2O_{10}S_2K_2$, calculated 668.1, found 668.5; $^1$H-NMR ($D_2O$): δ7.75–7.5 (m, 4H), 7.15–6.95 (m, 2H), 5.55 (s, 1H), 5.35 (s, 1H), 4.55 (t, 2H, J=6.5 Hz), 2.05–2.3 (m, 2H), 1.5–1.2 (m, 6H), 1.25 (t, 12H).

Synthesis of NHS-ester (6b)

The activation of (6a) to the NHS-ester (6b) was carried out in analogy with the activation of the bis-acid (3b) procedure (b), using one equivalent of NHS and 1,2 equivalents of DCC.

Analysis: M.P.>300° C.; $R_f$: 0.55 (RP-C18, methanol:water 2:1); FAB-MS, m/e ($M^+$, dianion) for $C_{36}H_{35}N_3O_{12}S_2K_2$, calculated 766.1, found 766.4; $^1$H-NMR ($D_2O$): δ7.85–7.5 (m, 4H), 7.15–6.9 (m, 2H), 5.55 (s, 1H), 5.35 (s, 1H), 4.45 (t, 2H, J=6.5 Hz), 2.7 (s, 4H) 2.05–2.35 (m, 2H), 1.5–1.2 (m, 6H), 1.25 (t, 12H).

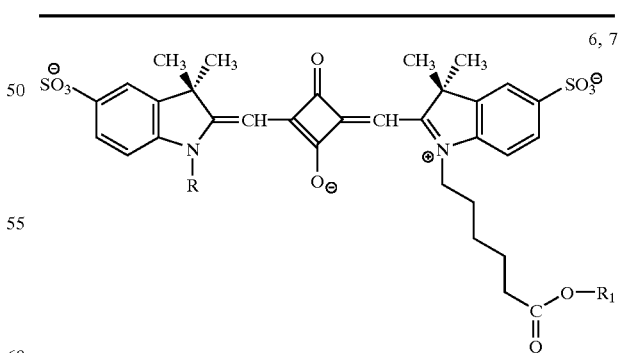

| Squaraine | R | R₁ |
|---|---|---|
| 6a | CH₃ | H |
| 6b | CH₃ | NHS |
| 7a | H | H |
| 7b | H | NHS |

EXAMPLE 4

Synthesis of 2-[N-(5-carboxypentyl)-3,3-dimethyl-5-sulfo-2-indolinylidene methyl]-4-[1,3,3-trimethyl-5-sulfo-2-indolinylidenemethyl]-cyclobutene diylium-1,3-diolate (7a)

Synthesis of mono-acid (7a)

1 g (2.4 mmol) of 1,2,3,3-tetramethylindoleninium-5-sulfonate (1c) was dissolved in 10 mL of ethanol containing 50 μl of triethylamine. The temperature of the reaction mixture was increased to 40° C., and 640 μl (2.9 mmol) of squaric acid dibutyl ester (2c) were slowly added. The reaction mixture was then heated to 60° C. and stirred for 4 h. After the mixture was cooled to room temperature, the solvent was removed under reduced pressure, and the yellow crystalline residue was used without further purification.

In the next step, 860 mg of 1-(ε-carboxypentyl)-2,3,3-trimethylindolenium-5-sulfonate (1a) in a butanol/toluene mixture (1/1 v:v) were added and refluxed for 5 h using a Dean-Stark trap. After the mixture was cooled, the solvents were removed under reduced pressure. The product was purified on preparative TLC (RP-18 $F_{254S}$) using methanol:water (2:1 v:v) as the eluent. 150 mg of the raw product were dissolved in 1 mL methanol and separated on a preparative TLC plate.

Yield: 50 mg (30%); M.P.>300° C.; $R_f$: 0.75 (RP-C18, methanol/water 2/1); FAB-MS m/e calculated for $C_{33}H_{34}N_2O_{10}S_2K_2$ ($M^{2-}$) 682.8, found 683.0; $^1$H-NMR ($D_2O$): δ7.70–7.55 (m, 4H), 7.20–7.00 (m, 2H), 5.50 (s, 1H), 5.40 (s, 1H), 4.45 (t, 2H, J=6.5 Hz), 4.00 (s, 3H), 2.05–2.30 (m, 2H), 1.50–1.25 (m, 6H), 1.20 (t, 12H); analysis: calculated for $C_{33}H_{34}N_2O_{10}S_2K_2$*$2H_2O$: C, 49.73; H, 4.81; N, 3.52. found: C, 49.60; H, 4.74; N, 3.58.

Synthesis of NHS-ester (7b)

The activation of (7a) to the NHS-ester (7b) was carried out in analogy with the activation of the bis-acid (3b) procedure b), using one equivalent of NHS and 1,2 equivalents of DCC.

EXAMPLE 5

Synthesis of 2,4-Bis[1,3,3-trimethyl-2-indolinylidenemethyl]cyclobutenediylium-1,3-dithiolate (9)

2,4-Bis[1,3,3-trimethyl-2-indolinylidenemethyl] cyclobutenediylium-1,3-dioxolate (8)

Squaraine dye (8) was synthesized according to Terpetschnig et al., Dyes & Pig. 21, 227 (1993).

Analysis: $^1$H-NMR (CDCl3, TMS): δ1.78 (s, 12H), 3.57 (s, 6H), 5.92 (s, 2H), 7.01(d, 2H), 7.16 (t, 2H), 7.28 (d, 2H), 7.35 (t, 2H); $λ_{max}$(abs)=633 nm (CHCl$_3$); $λ_{max}$(em)=653 nm (CHCl$_3$); ε=307,000 (CHCl$_3$) L/(mol*cm).

Dithio-squaraine (9)

0.32 g (0.75 mmol) of squaraine dye (8) and 0.40 g (0.90 mmol) of phosphorus pentasulfide $P_2S_5$ were refluxed in 6.5 mL of pyridine with stirring for 5 h. After cooling, the resulting precipitate was filtered, and washed with 3 mL of pyridine and 30 mL of ether. The precipitate was purified by column chromatography on Silcagel C-120 using chloroform as a solvent, and was recrystallized from pyridine.

Yield: 0.18 g (53%), before purification; M.P.=271° C.; sulfur analysis for $C_{28}H_{28}N_2S_2$, S (cal): 14.04%, S (found): 13.53%; $^1$H-NMR (CDCl3, TMS): δ1.75 (s, 12H), 3.83 (s, 6H), 6.21 (s, 2H), 7.09 (d, 2H), 7.21 (t, 2H), 7.27 (d, 2H), 7.36 (t, 2H); $λ_{max}$(abs)=658 nm (CHCl$_3$), $λ_{max}$(em)=707 nm (CHCl$_3$); ε=150,000 (CHCl$_3$) L/(mol*cm).

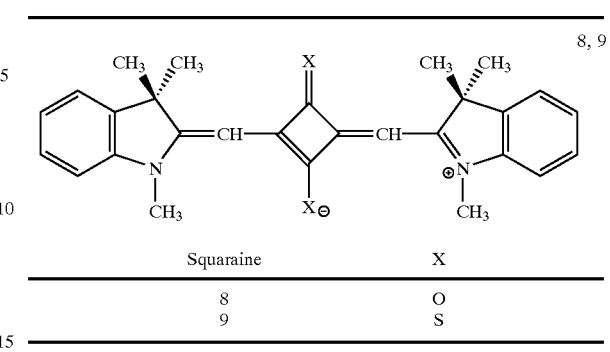

| Squaraine | X |
|---|---|
| 8 | O |
| 9 | S |

Synthesis of 2-[3,3-dimethyl-2-1(H) indolinylidenemethyl]4-[1-ethyl-benzoselanzolinylidene-methyl]cyclobutenediylium-1,3-dithiolate (11)

2-[3,3-dimethyl-2-1H)indolinylidenemethyl]4-[1-ethyl-benzoselenazolinylidene-ethyl]cyclobutenediylium-1,3-dioxolate (10c)

Synthesized according to Terpetschnig et al., Dyes & Pig. 21, 227 (1993).

1-[3'-Ethyl-2(3H)benzoselenazolylidene-2-methyl]3-ethoxycyclobuten-3,4-dione (10a)

15 mmol of N-ethyl-2-methylbenzoselenazolium iodite were added to a stirred hot solution of 10 mmol ethylsquarate and 2 mL triethylamine in 15 mL of ethanol. The solution was kept at 70–80° C. for 5 min, and then cooled to room temperature. The resulting yellow-to-red colored precipitate was isolated, washed with ethylether, and dried. The product was purified by column chromatography on silica gel using CHCl$_3$:EtOAc (9:1, v:v) as eluent.

Yield: 58%; M.P.=278–80° C.; $^1$H-NMR (D$_6$-DMSO): δ1.40 (t, 3H), 1.52 (t, 3H), 4.07 (q, 2H), 4.84 (q, 2H), 5.69 (s, 1H), 7.05 (d, 1H), 7.13 (t, 1H), 7.35 (t, 1H), 7.55 (d, 1H).

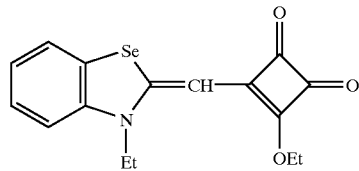

2-Hydroxy-1-[3'-ethyl-2(3H)benzoselanzolylidene-2'-methyl]cyclobuten-3,4-dione (10b)

5 mmol of (10a) were suspended in 20 mL of boiling ethanol, and dissolved on addition of 0.6 mL of 40% NaOH. The solution was kept at boiling for another 5 min and then cooled to room temperature. After addition of 6–7 mL of 2 M HCl, the ethanol solution was concentrated, and the resulting precipitate was collected and used without further purification.

Yield: 95%; M.P.=252–254° C.; $^1$H-NMR(D$_6$-DMSO): δ1.24 (t, 3H), 4.07 (q, 2H), 4.1 (q, 2H), 6.08 (s, 1H), 7.09 (t, 1H), 7.32 (m, 2H), 7.81 (d, 1H).

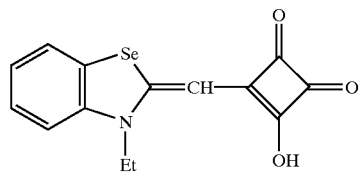

Squaraine (11a or 11b)

1 mmol of the squaric acid (10b) and 1 mmol of 2-methylene-1,3,3-trimethylindolenine or 2-methylene-3,3-dimethylindolenine (from Aldrich) were heated under reflux in a mixture of 20 mL toluene and 20 mL 1-butalnol. Water was removed azeotropically using a Dean-Stark trap. After 16 h, the reaction was cooled to room temperature, and the solvents were removed under vacuum. The residue was treated with ether, and the product was isolated by filtration. Further purification was achieved using column chromatography with chloroform-2-propanol mixtures as eluent.

Yield: 88% of (11a); M.P.=278–280 °C.; $^1$H-NMR (CDCl$_3$): δ1.45 (t, 3H), 1.77 (s, 6H), 3.46 (s, 3H), 4.23(q, 2H), 5.76 (s, 1H), 6.19 (s, 1H), 6.94(d, 1H), 7.09 (t, 1H), 7.31 (t, 1H), 7.32(d, 1H), 7.39 (d, 1H) 7.41 (t, 1H), 7.62 (d, 1H); $\lambda_{max}$ (abs)=657 nm (CHCl$_3$); $\lambda_{max}$(em)=675 nm (CHCl$_3$).

Yield: 80% of (11b); $^1$H-NMR(CDCl$_3$): δ1.5 (s, 9H), 4.25 (m, 2H), 5.45 (s 2H), 7.65–7.15 (m, 8H), 12.2 (s, 1H).

Thiosquaraine (12a) and (12b)

40 mg (0.087 mmol) of 2-hydroxy-1-[3'-ethyl-2(3H)benzoselanzolylidene-2'methyl]cyclobuten-3,4-dione (10a) and 70 mg (0.144 mmol) of P$_2$S$_5$ were refluxed for 5 h in 2 mL of pyridine under stirring. The solvent was removed under reduced pressure, and the residue was treated with chloroform. Chloroform was removed under reduced pressure, and the product was purified using preparative TLC, again using chloroform as the solvent system.

Analysis: $\lambda_{max}$(abs)=687 nm (CHCl$_3$); $\lambda_{max}$(em)=724 nm (CHCl$_3$).

In an analogous procedure, 20 mg of squaraine (10b) and 30 mg of phosphor pentasulfide P$_2$S$_{10}$ were reacted in 1.5 mL of pyridine for 4 h. The compound (10d) was purified as described above.

Analysis: $\lambda_{max}$(abs)=690 nm (CHCl$_3$); $\lambda_{max}$(em)=724 nm (CHCl$_3$).

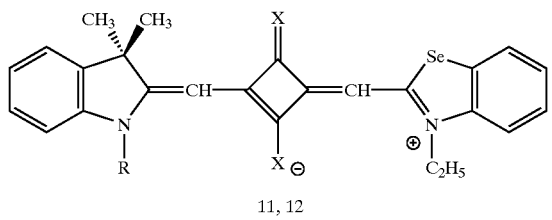

11, 12

| Squaraine | R | X |
|---|---|---|
| 11a | CH$_3$ | O |
| 11b | H | O |
| 12a | CH$_3$ | S |
| 12b | H | S |

EXAMPLE 6

Synthesis of 2,4-Bis[N-(5-carboxypentyl)-3,3-dimethyl-5-sulfo-2-indolinylidene methyl] cyclobutenediylium-1,3-dithiolate (13)
1,3-Dithiosquaric acid disodium salt (2c)
1,3-Bis(dimethylamino)-squaric acid

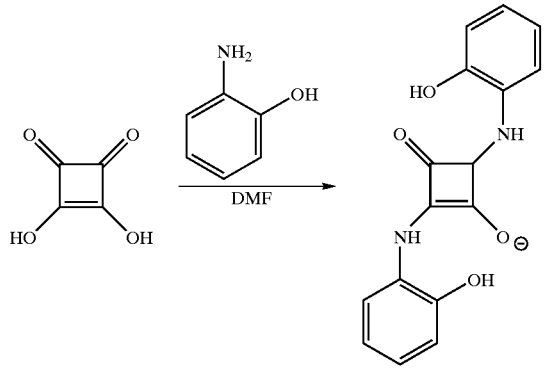

A solution of 20 mL of DMF, 4 g (35 mmol) of squaric acid, and 7.2 g (66 mmol) of o-aminophenole was refluxed for 1.5 h using a mechanical stirrer. The yellow precipitate was filtered off, washed with ether, and dried in a desiccator over CaCl$_2$. The product was used without further purification.

Yield: 4.7 g (80%), yellow powder.
1,3-Thiosquaric acid, disodium salt (2c)

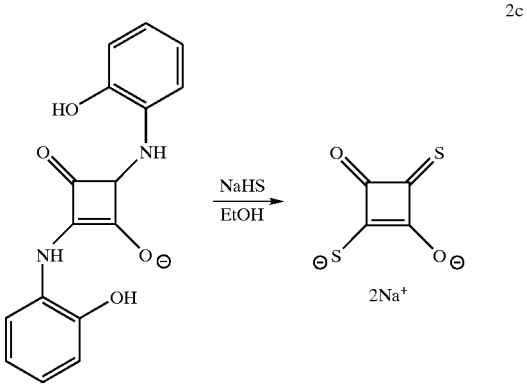

2c 3.52 g (21 mmol) of 1,3-bis(dimethylamino)squaric acid and 1.30 g (35 mmol) of sodium hydrogenesulfide monohydrate were refluxed for 30 min in 50 mL of dry ethanol. An orange precipitate was formed, which was filtered off and washed with ethanol, acetonitrile, and ether. The product was dried in a desiccator over CaCl$_2$.

Yield: 2.4 g (60%), orange powder.
Thio-squaraine (13)

300 mg (0.64 mmol) of 1-(ε-carboxypentyl)-2,3,3-trimethylindolenium-5-sulfonic acid potassium salt (1a) (synthesized according to Mudjumdar et al. (1993)) and 62 mg (0.33 mmol) of 1,3-thiosquaric acid disodium salt (2c) were suspended in 16 mL of 1:1 butanol:toluene (v:v). The solution was heated to reflux for 4 h. The reaction was controlled by TLC (RP-C18, methanol:water 2:1, v:v), which showed a major spot at R$_f$: 0.75 for the diacid (13) and a minor spot at R$_f$: 0.55 for the dibutylester due to the esterification of the carboxylic acid groups in BuOH. After removal of toluone at reduced pressure, the reaction mixture was cooled to 4° C., and the precipitate was filtered. The crude product was redissolved in a mixture of 2.5 mL of methanol and 1 mL of water, and purified on an preparative RP-C18 plate using methanol:water (2:1, v:v) as eluent. The major band was collected, and the product was extracted using methanol as solvent.

Yield: 67 mg (9.6%); $R_f$: 0.75 (RP-C18, methanol:water 2:1); ESI-MS, m/e (M$^+$, di-acid) for $C_{38}H_{42}N_2O_{10}S_4H_2$, calculated 816.9, found 817.5 $^1$H-NMR (D$_2$O): δ8.00 (2H, s), 7.90 (2H, d), 7.80 (2H, d), 5.75 (1H, s), 4.35 (4H, t), 2.15 (4H, t), 1.85 (4H, m), 1.55 (4H, m), 1.50 (12H, s), 1.35 (4H, m); $\lambda_{max}$(abs)=642 nm (HSA-conjugate in PBS); $\lambda_{max}$(em)= 654 nm (HSA-conjugate in PBS); ε=68.000 (L/mol*cm).

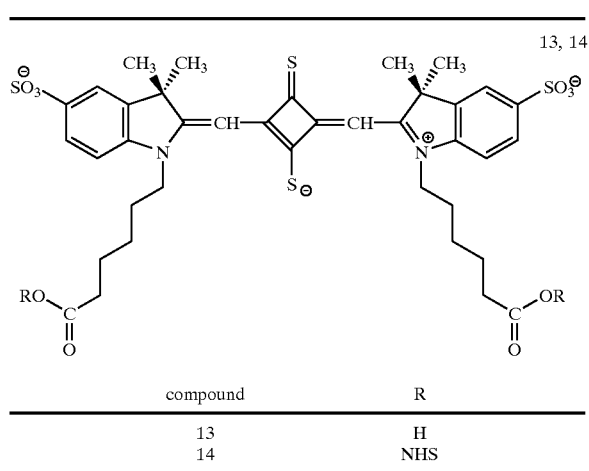

13, 14

| compound | R |
|---|---|
| 13 | H |
| 14 | NHS |

Synthesis of bis-NHS-ester (14)

0.5 mL of anhydrous DMF was added to a mixture of 7.3 mg (0.009 mmol) of b-acid (13), 10.5 mg (0.05 mmol) of dicyclohexylcarbodiimide (DCC), and 2 mg (0.018 mmol) of N-hydroxysuccinimide (NHS). The solution was stirred for 24 h at room temperature and filtered. The solvent was removed in vacuum, and the product was triturated with ether and dried over P$_2$O$_5$.

Yield, 7 mg (91%); $R_f$: 0.82 (RP-C18, methanol/water 2/1).

EXAMPLE 7

Synthesis of 2,4-Bis[N-(ε-butoxycarbonylpentyl)-3, 3-dimethyl-5-sulfo-2-indolinylidene methyl] cyclobutenediylium-3-dicyanomethylene-1-oxolate (15)

3-Dicyanomethylene-2,4-dibutyl-squarate (2d)

3-Dicyanomethylene-2,4-dibutyl-squarate (2d) was prepared according to Gerecht et al. (1984).

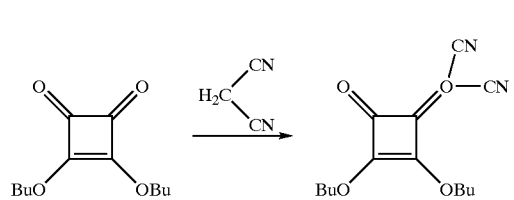

2d 2.16 mL (10 mmol) of squaric acid dibutylester (2c) were dissolved in 40 mL of THF. 660 mg (10 mmol) of malonedinitrile were added under stirring. A solution of 1.64 mL of triethylamine in 3 mL of THF was then added, and the mixture was stirred at room temperature for 15 h. The solvent was removed under reduced pressure, and a yellow-brown oil remained. The raw product is purified by MPLC using silica gel as the stationary phase and methanol as eluent.

Yield: 173 mg (63%) of (2d).

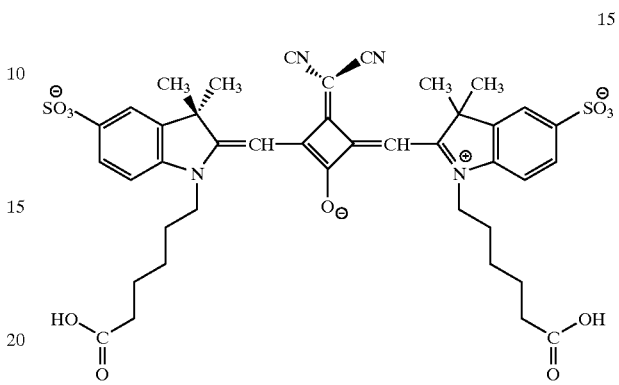

15

472 mg of 1-(ε-carboxypentyl)-2,3,3-trimethylindolenium-5-sulfonic acid potassium salt (1a) and 137 mg of malondinitrile squaric acid dibutylester (2d) were refluxed in 25 mL of butanol:toluene (1:1, v:v) for 4 h using a Dean-Stark trap. After the mixture was cooled to room temperature, the solvents were removed in vacuum, and the raw product was triturated with ether and dried. The raw product was purified by preparative thin-layer chromatography on RP-18 glass plates using a methanol/water mixture (2/1, v:v) as eluent. The blue-green band with an $R_f$ of 0.55 was collected.

Yield: 32%; FAB-MS m/e calculated for $C_{41}H_{44}N_4O_{11}S_2K_2$ (M$^{2-}$) 832.9, found 633.2. IR (KBr): 2100 cm$^{-1}$ (CN). $^1$H-NMR (D$_2$O): δ8.00 (2H, s), 7.90 (2H, d), 7.75 (2H, d), —C$\underline{H}$= is exchanged, 4.45 (4H, t), 2.10(4H, t), 1.85 (4H, m), 1.55 (4H, m), 1.45 (12H, s), 1.35 (4H, m); $\lambda_{max}$(abs)=667 nm (PBS), $\lambda_{max}$(em)=685 nm (PBS), (4%); $\lambda_{max}$(abs)=687 nm (PBS+HSA), $\lambda_{max}$(em)= 704 nm (PBS+HSA), (8%), ε=110.000 L/mol*cm (H$_2$O).

EXAMPLE 8

Synthesis of a Reactive Croconium-dye
Croconium dye (16)

0.8 g of 1-(δ-sulfonatobutyl)-2-methylbenzthiazolium iodide (as described in U.S. Pat. No. 3,793,313) and 0.15 g of croconic acid (Aldrich) were suspended in a mixture of 10 mL of pyridine and 0.3 mL of triethylamin gelöst. The mixture was stirred overnight at room temperature, the solvent was removed at reduced pressure, and the residue was triturated with methanol filtered and dried.

Yield: 0.6 g (50%).

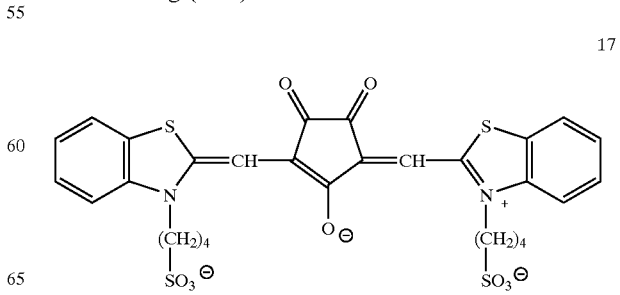

17

Synthesis of the sulfonyl chloride (17)

0.1 g of (16) and 0.3 g of $PCl_5$ were mixed in a mortar, and the mixture was heated in a round bottom flask for 30 min to 100° C. 10 mL of toluene were then added, and the mixture was stirred for another 45 min at room temperature. The reaction mixture was transferred to a separation funnel, $CHCl_3$ was added, and the unreacted $PCl_5$ was removed by extraction with water. The organic layers were combined, and the solvents were removed under reduced pressure. The product was dried under vacuum.

Yield: 0.05 g.

EXAMPLE 9

Asymmetric Thiosquaraine and Dicyanomethylene-squaraines

Synthesis of mono-substituted thiosquaraine and dicyanomethylen-squaraine derivatives The following are important intermediates for the synthesis of asymmetric squaraine dyes and can be synthesized using either squaric acid or squaric ester derivatives as starting materials. A general procedure for the synthesis of two classes of asymmetric squaraine analogs is given below.

1 mmol of 1-(ε-carboxypentanyl)-2,3,3-trimethylindolenium-5-sulfonate was dissolved in 10 mL of ethanol containing 100 μL of triethylamine. The mixture was warmed to 40° C., and 1.1 mmol of either dicyanomethylene-squaric acid dibutyl ester (2d) or 1,3-dithio squaric acid disodium salt (2c) were added in small portions. The reaction mixture was then heated to 60° C. and stirred for 4 h. After the mixture was cooled to room temperature, the solvent was removed under reduced pressure. The residue was redissolved in ethanol, 5 mL of 0.1 M HCl were added and the mixture was refluxed for 10 min. After cooling, the solvents were removed, and the residue was washed several times with either ether or chloroform.

| Squaraine-derivative | R | R1 |
|---|---|---|
| Dicyano-methylene | C(CN)₂ | OH |
| Dithio- | S | SH |

General synthesis procedure for asymmetric thiosquariane and methylenesquariane dyes The above intermediates were heated under reflux with 1 mmol of 1,2,3,3-tetramethylindoleninium-5-sulfonate in a butanol:toluene mixture (1:1 v/v) for 5 h using a Dean-Stark trap. After cooling, the solvents were removed under reduced pressure. The product can be purified on preparative TLC (RP-18 $F_{254S}$) using methanol:water (2:1 v:v) as the eluent.

Yield: 25–30% of asymmetric compound.

Synthesis scheme for an asymmetric thiosquaraine dye

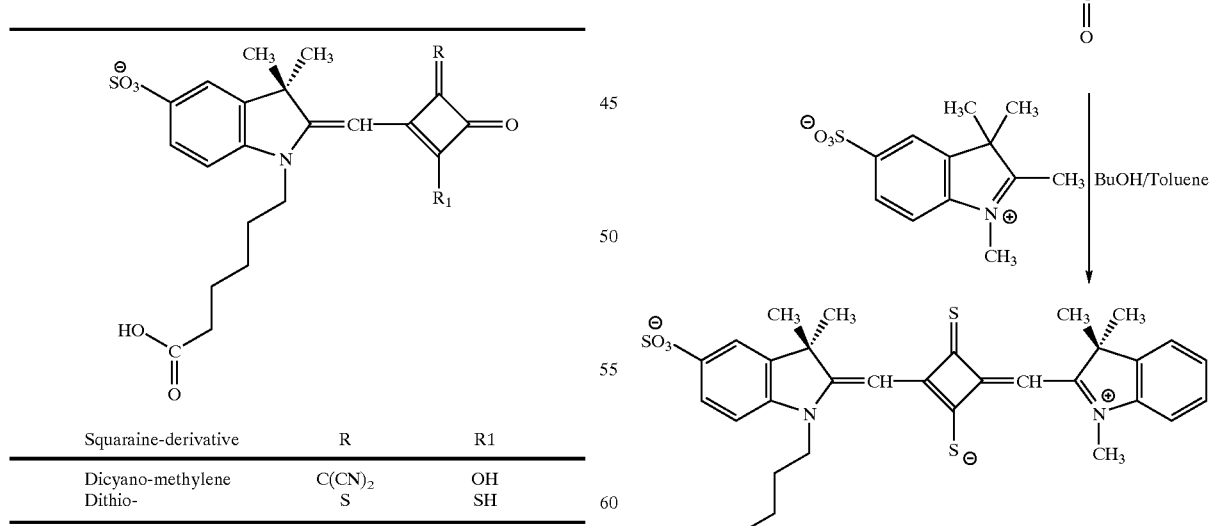

EXAMPLE 10
Additional Structures of Thiosquariane, Methylenesquaraine, and Croconium Dyes
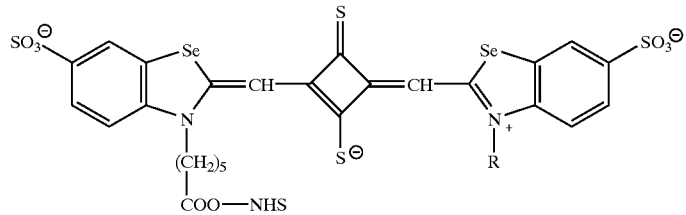
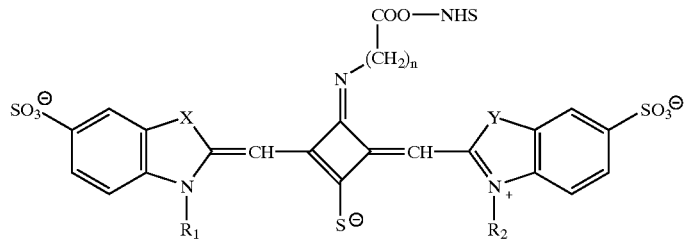
n = 1–30
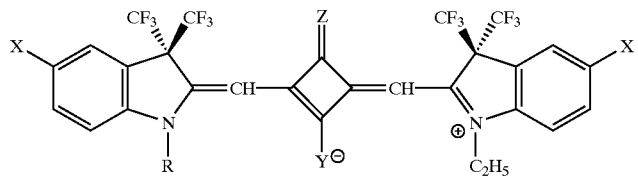
X = H, F, Cl, Br, I, —CH$_2$NH$_2$, SO$_3^-$, COOH, CONHS etc.;
Y = O, S; Z = O, S, NR$^1$, CR$^2$R$^3$;
R, R$^1$, R$^2$, R$^3$ = H, (CH$_2$)$_n$X, (CF$_2$)$_n$X, n = 1–30; R$^2$, R$^3$ = CN, COOR
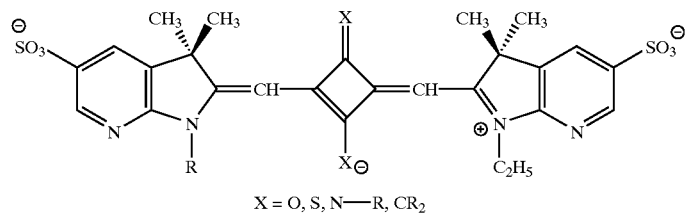
X = O, S, N—R, CR$_2$
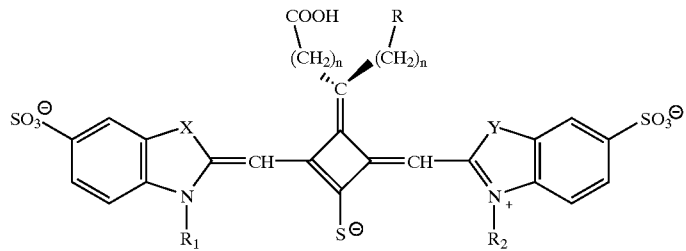
n = 1–30
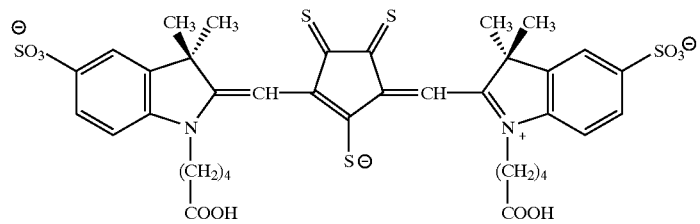

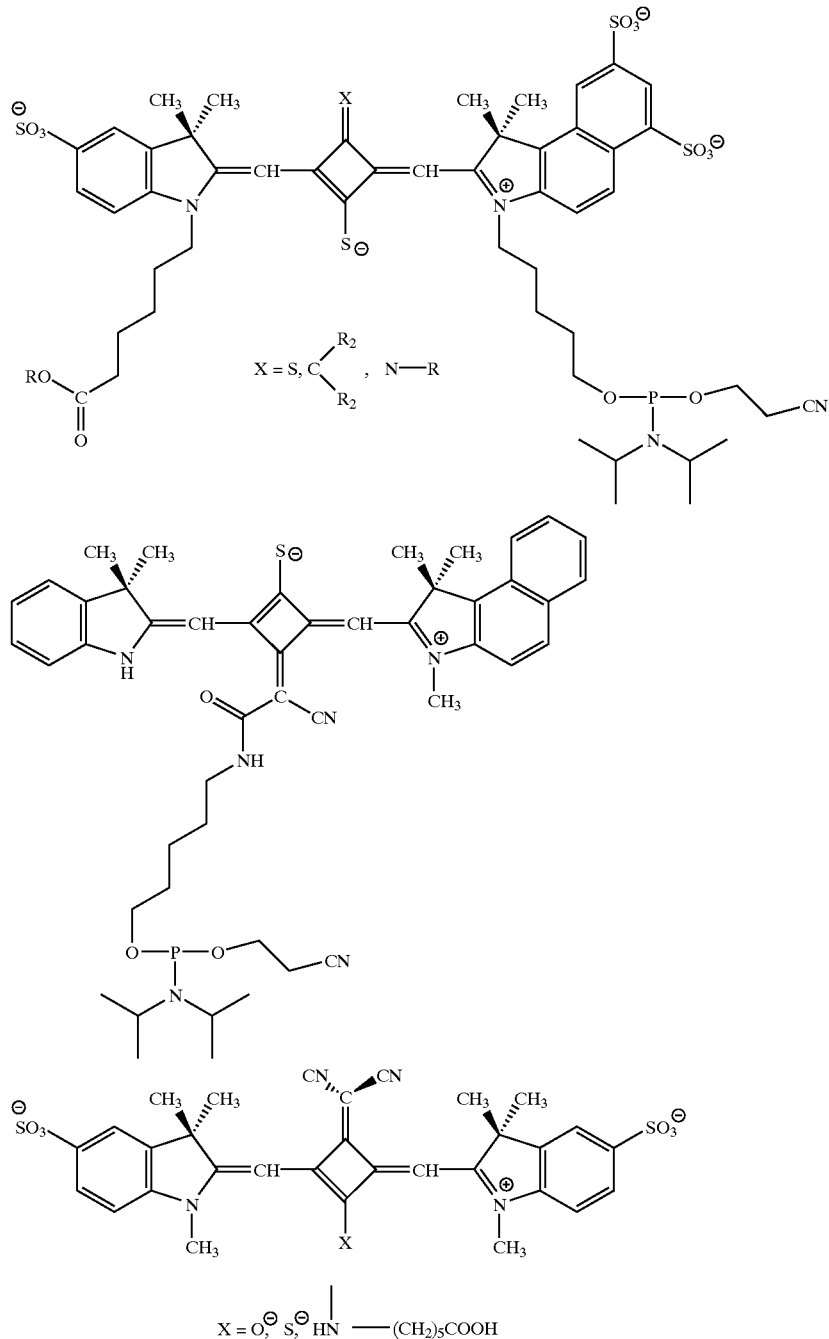

Example 10 shows representative structures of squaraine dyes. The fluorinated versions may exhibit higher photostability and higher quantum yields than the non-fluorinated versions. Other structures may contain reactive functional groups in the central squaraine ring for covalent attachment to carrier molecules. To introduce an amino-function into the squaraine ring, the squaraine or substituted squaraine may be converted into a mono-ester (X=OMe, OBu), where Me is methyl and Bu is butyl. The mono-ester then may be reacted with the amine or an amino acid derivative to give the amino derivative. This mechanism offers a convenient way of converting a nonreactive squaraine dye into a reactive analog. Water-insoluble, hydrophobic versions of these structures as shown above (lacking the sulfonic groups) may be used in DNA sequencing and for covalent or noncovalent reaction with polymers or proteins.

EXAMPLE 11

General Protein Labeling Procedures and Determination of Dye-to-Protein Ratios

Protein labeling reactions were carried out using a 50 mM bicarbonate buffer (pH 9.1). A stock solution of 1 mg of dye in 100 μL of anhydrous DMF was prepared. 10 mg of protein were dissolved in 1 mL of 100 mM bicarbonate buffer (pH 9.1). Dye from the stock solution was added, and the mixture was stirred for 24 h at room temperature.

Unconjugated dye was separated from labeled proteins using gel permeation chromatography with Sephadex G50 (0.5 cm×20 cm column) and a 22 mM phosphate buffer solution (pH 7.3) as the eluent. The first colored band contained the dye-protein conjugate. A later blue band with a much higher retention time contained the separated free dye. A series of labeling reactions as described above were set up to obtain different dye-to-protein ratios. Compared to the free forms, the protein-bound forms of the dyes show distinct changes in their spectral properties.

Protein concentration was determined using the BCA Protein Assay Reagent Kit from Pierce (Rockford, Ill.). The dye-to-protein ratio (D/P) gives the number of dye molecules covalently bound to the protein.

Covalent attachment of NHS-ester (14) to polyclonal anti-HSA

385 μl (5.2 mg/mL) of anti-HSA were dissolved in a 750 μl bicarbonate buffer (0.1 M, pH 9.0). 1 mg of NHS-ester (14) was dissolved in 50 μL of DMF and slowly added to the above-prepared protein solution with stirring. After 20 h of stirring, the protein-conjugate was separated from the free dye using Sephadex G50 and a phosphate buffer (22 mM, pH 7.2). The first blue band that was isolated contained the labeled conjugate.

Conjugation of (14) to HSA 0.5 mg of (14) in 50 μl of DMF were slowly added to a stirred solution of 5 mg of HSA in 750 μl of bicarbonate buffer (0.1 M, pH 9.0). The mixture was stirred for another 6 h at room temperature. The mixture was dialyzed against a phosphate buffer (22 mM, pH 7.2) using a dialysis membrane (1500 FT, Union Carbid) with a cutoff of 10.000.

Analysis: $\lambda_{max}$(abs)=642 nm (PBS); $\lambda_{max}$(em)=654 nm (PBS).

Similar reactions were performed using the other reactive dyes.

Fluorescence decay times of various dyes and their conjugates

The following table shows fluorescence decay times of various dyes and their conjugates. The experimental conditions included (1) excitation at 600 nm, using a rhodamine B dye laser, (2) emission observed at 660 nm, using an interference filter having a 10 nm band pass, and (3) temperature of 20° C.

| Sample | Decay time [ns] | Amplitude | Fractional Intensity | Mean lifetime [ns] | Chi square |
|---|---|---|---|---|---|
| 3a | 0.21 | 0.752 | 0.496 | 0.43 | 3.7 |
|  | 0.65 | 0.248 | 0.504 |  |  |
| 4 | 0.20 | 0.558 | 0.286 | 0.51 | 3.8 |
|  | 0.64 | 0.442 | 0.714 |  |  |
| 3b-HSA | 0.18 | 0.676 | 0.142 |  |  |
|  | 0.96 | 0.089 | 0.097 | 2.26 | 1.7 |
|  | 3.81 | 0.235 | 0.761 |  |  |
| 13-HSA | 0.011 | 0.865 | 0.036 |  |  |
|  | 0.768 | 0.068 | 0.201 | 2.44 | 5.22 |
|  | 2.99 | 0.067 | 0.764 |  |  |
| Cy5 | 1.02 | 1 | 1 | 1.01 | 2.1 |
| Cy5-hCG | 0.16 | 0.408 | 0.071 | 1.33 | 2.8 |
|  | 1.41 | 0.592 | 0.929 |  |  |

Spectral properties and dye-to-protein ratios for various reactive squaraine dyes and their conjugates Spectral properties and dye-to-protein ratios were determined for various reactive squaraine dyes and their conjugates. FIG. 1 shows absorption (excitation) and emission spectra for (13)-HSA in PBS. The following table summarizes data for (13)-HSA and various other reactive squaraine dyes and their conjugates in PBS.

| Squaraine | $\lambda_{max}$ (abs) [nm] | $\lambda_{max}$ (em) [nm] | ε [L/mol*cm] | Q.Y. [%] | D/P [mol/mol] |
|---|---|---|---|---|---|
| 3b | 635 | 642 | 180.000 | 13 | — |
| 3b-HSA | 642 | 653 | — | 60–70 | 1 |
| 6a | 627 | 647 | 100.000 | 3 | — |
| 7 | 634 | 646 | 120.000 | 13 | — |
| 7-HSA | 635 | 660 | — | 50 | 0.5 |
| 13 | 630 | 649 | 66.000 | 5 | — |
| 13-HSA | 642 | 654 | — | 60–70 | 0.8 |
| 15 | 667 | 685 | 110.000 | 4 | — |
| 15-HSA | 685 | 704 | — | n.d. | n.d. |

EXAMPLE 12

Description of Applications of the Invention

Photoluminescent compounds provided In addition to the compounds the invention provides also a number of methods for utilizing these compounds in various assay formats.

The assay may be a competitive assay that includes a recognition moiety, a binding partner, and an analyte. Binding partners and analytes may be selected from the group consisting of biomolecules, drugs, and polymers. In some competitive assay formats, one or more components are labeled with photoluminescent compounds in accordance with the invention. For example, the binding partner may be labeled with such a photoluminescent compound, and the displacement of the compound from an immobilized recognition moiety may be detected by the appearance of fluorescence in a liquid phase of the assay. In other competitive assay formats, an immobilized enzyme may be used to form a complex with the fluorophore-conjugated substrate.

The binding of antagonists to a receptor can be assayed by a competitive binding method in so called ligand/receptor assays. In such assays, a labeled antagonist competes with an unlabelled ligand for the receptor binding site. One of the binding partner can be, but not necessarily does has to be immobilized. Such assays can also be performed in microplates. Immobilization can be achieved via covalent attachment to the well wall or to the surface of beads.

Other preferred assay formats are immunological assays. There are several types assay formats. Competitive binding assays, in which labeled and unlabeled antigens compete for the binding sites on the surface of an antibody (binding material). Typically, there are incubation times required to provide sufficient time for equilibration. Such assays can be performed in a heterogeneous or homogeneous fashion.

Sandwich assays use secondary antibodies and access binding material is removed from the analyte by a washing step.

Other types of reactions include binding between avidin and biotin, protein A and immunoglobulins, lectins and sugars (e.g., concavalin A and glucose).

Photoluminescent compounds described here also may be used to sequence nucleic acids and peptides. For example, fluorescently labeled oligonucleotides may be used to trace DNA fragments.

Other applications of labeled DNA primers besides for DNA sequencing are in fluorescence in-situ hybridization methods (FISH) and for single nucleotide polymorphisms (SNPs) applications.

Multicolor labeling experiments allow different biochemical parameters to be monitored simultaneously. For this purpose, two or more fluorophores are introduced into the biological system to report on different biochemical functions. The technique can be applied to fluorescence in-situ hybridization (FISH), DNA sequencing, fluorescence microscopy, and flow cytometry. One way to achieve multicolor analysis is to label biomolecules such as nucleotides, proteins or DNA primers with different fluorescent markers and distinct fluorescence properties. Fluorophores with narrow emission bandwidths are preferred for multicolor labeling, because they have only a small overlap with the other dyes and hence increase the number of dyes possible in a multicolor experiment. Importantly, the emission maxima have to be well separated from each other to allow sufficient resolution of the signal. A suitable multicolor triplet of fluorophores would include Cy3, TRITC, and a photoluminescent compound as described herein, among others.

The simultaneous use of FISH (fluorescence in-situ hybridization) probes in combination with different fluorophores is useful for the detection of chromosomal translocations, for gene mapping on chromosomes, and for tumor diagnosis, to name only a few. One way to achieve simultaneous detection of multiple sequences is to use combinatorial labeling. Up to seven different DNA targets can be simultaneously visualized by using a combination of haptenated DNA probes (e.g. biotin, digoxigenin or dinitrophenol) with three sets of distinguishable fluorophores showing emission in the green (fluorescein), red (Texas Red), and blue (7-amino-4-methyl-coumarin-3-acidic acid or Cascade Blue) (Ried et al., Proc. Natl. Acad. Aci. USA 89, 1388–1392 (1992)). Three labeled DNA probes can be visualized by the distinct spectra of the three fluorescent markers, while four others will appear as fluorophore mixtures, e.g. probe 4 (fluorescein and rhodamine); probe 5 (fluorescein and Cascade Blue); probe 6 (rhodamine and cascade Blue); and probe 7 (fluorescein, rhodamine and Cascade Blue).

The second way is to label each nucleic acid probe with a fluorophore with distinct spectral properties. Similar conjugates can be synthesized from this invention and used in a multicolor multisequence analysis approach.

The luminescent compounds of the invention can also be used for screening assays for a combinatorial library of compounds. The compounds can be screened for a number of characteristics, including their specificity and avidity for a particular recognition moiety.

Assays for screening a library of compounds are well known. A screening assay is used to determine compounds that bind to a target molecule, and thereby create a signal change which is generated by a labeled ligand bound to the target molecule. Such assays allow screening of compounds that act as agonists or antagonists of a receptor, or that disrupt a protein-protein interaction.

Other screening assays may be based on compounds that affect the enzyme activity. For such purposes, quenched enzyme substrates of the invention could be used to trace the interaction with the substrate. In this approach, the cleavage of the fluorescent substrate leads to a change in spectral properties such as the excitation and emission maxima, intensity, and/or lifetime, which allows the assay to discriminate between free and bound fluorophore.

There are limitations to the use of these compounds as labels. Only a limited number of dyes can be attached to a biomolecule without altering the fluorescence properties of the dyes (e.g., quantum yields, emission characteristics, etc.) and/or the biological activity of the bioconjugate. Typically, quantum yields are reduced at higher degrees of labeling. Encapsulation into beads offers a means to overcome the above limitations for the use of such dyes as fluorescent markers. Fluorescent beads and polymeric materials are becoming increasingly attractive as labels and materials for bioanalytical and sensing applications. Various companies offer particles with defined sizes ranging from nanometer to micrometer. Noncovalent encapsulation in beads may be achieved by swelling the polymer in an organic solvent, such as toluene or chloroform, containing the dye. Covalent encapsulation may be achieved usingreactive functions on both the polymer and the dyes. In general, hydrophobic versions of the invention would be used for the noncovalent encapsulation in polymers, and one or more dyes could be introduced at the same time. Surface-reactive fluorescent particles allow covalent attachment to molecules of biological interest, such as antigens, antibodies, receptors, etc.

Analytes

The invention can be used to detect an analyte that interacts with a recognition moiety in a detectable manner. As such, the invention can be attached to a recognition moiety which is known to those of skill in the art. Such recognition moieties allow the detection of specific analytes. Examples are pH-, or potassium sensing molecules, e.g., synthesized by introduction of potassium chelators such as crown-ethers (aza crowns, thia crowns etc). Calcium-sensors based on BAPTA (1,2-Bis(2-aminophenoxy)ethan-N,N,N',N'-tetra-aceticacic) as the chelating species are frequently used to trace the intracellular ion concentrations. The combination of a compound of the invention and the calcium binding moiety BAPTA can lead to new long-wavelength absorbing and emitting Ca-sensors which could be used for determination of intra- and extracellular calcium concentrations (Akkaya et al., Tetrahedron Lett. 38, 4513–4516 (1997)).

Fluorescence Methods

These compounds of the new invention can be detected applying commonly used intensity based fluorescent methods. The squaraine dyes are known to have lifetimes in the range of hundreds of ps to a few ns (see Table). The nanosecond lifetime and long-wavelength absorption and emission of these dyes when bound to proteins would allow them to be measured with inexpensive instrumentation using laser diodes for excitation and avalanche photodiodes for detection. Typical assay based on the measurement of the fluorescence lifetime as a parameter are FRET (fluorescence resonance energy transfer) assays. The binding between a fluorescent donor labeled species (typically an antigen) and a fluorescent acceptor labeled species are accompanied by a change in the intensity and the fluorescence lifetime. The lifetime can be measured using intensity- or phase-modulation-based methods (J. R. Lakowicz, Principles of Fluorescence Spectroscopy (1983)).

Squaraine dyes exhibit high intrinsic polarization in the absence of rotational motion, making them useful as tracers in fluorescence polarization (FP) assays. Fluorescence polarization immunoassays (FPI) are widely applied to quantify low molecular weight antigens. The assays are based on polarization measurements of antigens labeled with fluorescent probes. The requirement for polarization probes used in FPIs is that emission from the unbound labeled antigen be depolarized and increase upon binding to the antibody. Low molecular weight species labeled with the compounds of the invention can be used in such binding assays, and the unknown analyte concentration can determined by the change in polarized emission from the fluorescent tracer molecule.

Compositions and Kits

The invention also provides compositions, kits and integrated systems for practicing the various aspects and embodiments of the invention, including producing the novel compounds and practicing of assays.

The materials, methods and applications of the invention are exemplified by the following description of the synthesis and the spectral properties of the compounds.

The synthesis and spectral characterization of a squaraine derivative for covalent attachment to biomolecules was already reported. Squaraines, which are 1,3-disubstituted squaric acid derivatives, show high absorption coefficients ($\epsilon > 200.000$ l mol$^{-1}$ cm$^{-}$) in the red region, display a high photostability, and allow the introduction of reactive functional groups such as NHS esters. These dyes exhibit good quantum yields on binding to proteins. The hydrophilic character of the dyes can be improved by introducing sulfonic acid groups.

Hydrophobic versions of the invention can be used for covalent or noncovalent encapsulation into beads and nanoparticles. Such compositions may help to circumvent some of the limitations of the hydrophilic versions of the invention.

The advantages of fluorescence detection at long wavelength excitation are the decreased autofluorescence from cells and tissues and the use of inexpensive laser light sources such as diode lasers operating at 635, 645, and 650 nm. The autofluorescence of biological samples decreases with increasing wavelength, particularly beyond 600 nm. Only a few fluorescent probes exist that absorb in the red or near infrared (NIR) region and even fewer of them are available in a reactive form. Amine-reactive functionalities such as isothiocyanate and N-hydroxysuccinimide esters and thiol-reactive iodoacetamide and maleimide groups can be used to covalently attach marker molecules to drugs, DNA, antibodies or synthetic polymers.

EXAMPLE 13

Selected aspects of the invention also may be described as recited in the following numbered paragraphs:

1. A composition of matter comprising:

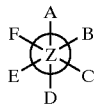

wherein:
(a) Z is a four, five, or six-member aromatic ring;
(b) A, B, C, D, E, and F are substituents of Z, wherein F is absent when Z is a five-member ring, and wherein E and F are absent when Z is a four-member ring;
(c) A, B, C, D, E, and F may be present in any order, and each of A, B, C, D, E, and F are bound to Z by a single or double bond;
(d) A is selected from the group consisting of S, Se, Te, and C(R$^a$)(R$^b$), wherein each of R$^a$ and R$^b$ is selected from the group consisting of carboxylic acid, cyano, carboxamide, carboxylic ester, and aliphatic amine groups;
(e) B is selected from the group consisting of W$^1$ and W$^2$, wherein W$^1$ and W$^2$ are given by

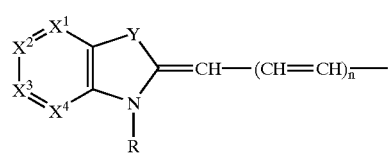

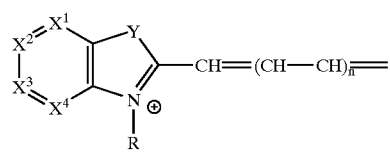

(f) each of C, D, E, and F, unless absent according to (b), is selected from the group consisting of O, S, Se, Te, N—R$^c$, N(R$^d$)(R$^e$), and C(R$^f$)(R$^g$), wherein each of R$^c$, R$^d$, and R$^e$ is selected from the group consisting of aliphatic, heteroatom-substituted aliphatic, polyether, aromatic, reactive aliphatic, and reactive aromatic groups, R$^f$ and R$^g$ being selected from the group consisting of carboxylic acid, cyano, carboxamide, carboxylic ester, and aliphatic amine groups;
(g) n is selected from the group consisting of 0, 1, and 2;
(h) Y is selected from the group consisting of O, S, Se, Te, N—R$^h$, and C(R$^i$)(R$^j$), wherein R$^h$ is selected from the group consisting of H, aliphatic groups, alicyclic groups, aromatic groups, and reactive aliphatic groups, and wherein each of R$^i$ and R$^j$ is selected from the group consisting of aliphatic and reactive aliphatic groups;
(i) R is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;
(j) each of X$^1$, X$^2$, X$^3$, and X$^4$ is selected from the group consisting of N, O, S, and C—R$^k$, wherein R$^k$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and
(k) each H may be independently replaced by a fluorine.

2. The composition of paragraph 1, wherein Z is based on squaric acid, croconic acid, or rhodizonic acid.
3. The composition of paragraph 1, wherein A is S.
4. The composition of paragraph 1, wherein Z is a four member ring.
5. The composition of paragraph 4, wherein each of C and D are O.
6. The composition of paragraph 4, wherein at least one of C and D are S.
7. The composition of paragraph 1, wherein R is C$_5$H$_8$O$_2$N$_a$.

8. A composition of matter comprising:

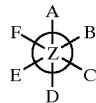

wherein:
(a) Z is a four, five, or six-member aromatic ring;
(b) A, B, C, D, E, and F are substituents of Z, wherein F is absent when Z is a five-member ring, and wherein E and F are absent when Z is a four-member ring;
(c) A, B, C, D, E, and F may be present in any order, and each of A, B, C, D, E, and F are bound to Z by a single or double bond;
(d) B is selected from the group consisting of $W^1$ and $W^2$, wherein $W^1$ and $W^2$ are given by

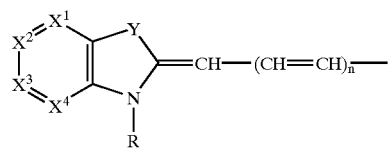

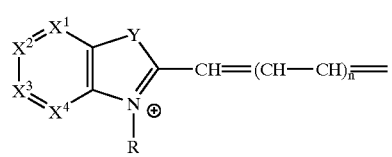

(e) each of A, C, D, E, and F, unless absent according to (b), is selected from the group consisting of O, S, Se, Te, N—$R^c$, N($R^d$)($R^e$), and C($R^f$)($R^g$), wherein each of $R^c$, $R^d$, and $R^e$ is selected from the group consisting of aliphatic, heteroatom-substituted aliphatic, polyether, aromatic, reactive aliphatic, and reactive aromatic groups, $R^f$ and $R^g$ being selected from the group consisting of carboxylic acid, cyano, carboxamide, carboxylic ester, and aliphatic amine groups;
(f) n is selected from the group consisting of 0, 1, and 2;
(g) Y is selected from the group consisting of O, S, Se, Te, N—$R^h$, and C($R^i$)($R^j$), wherein $R^h$ is selected from the group consisting of H, aliphatic groups, alicyclic groups, aromatic groups, and reactive aliphatic groups, and wherein each of $R^i$ and $R^j$ is selected from the group consisting of aliphatic and reactive aliphatic groups;
(h) R is selected from the group consisting of H, F, Cl, Br, I, aliphatic groups comprising 3 or more carbons, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;
(i) each of $X^1$, $X^2$, $X^3$, and $X^4$ is selected from the group consisting of N, O, S, and C—$R^k$, wherein $R^k$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and
(j) each H may be independently replaced by a fluorine.

9. The composition of paragraph 8, wherein Z is based on squaric acid, croconic acid or rhodizonic acid.

10. The composition of paragraph 8, wherein each of at least two of A, C, and D is O.

11. The composition of paragraph 8, wherein R is is $C_5H_8O_2N_a$.

12. A composition of matter comprising a photoluminescent compound, the photoluminescent compound comprising:

wherein:
(a) Z is a four, five, or six-member aromatic ring;
(b) A, B, C, D, E, and F are substituents of Z, wherein F is absent when Z is a five-member ring, and wherein E and F are absent when Z is a four-member ring;
(c) A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;
(d) each of B and C is selected from the group consisting of $W^1$ and $W^2$, wherein $W^1$ and $W^2$ are given by

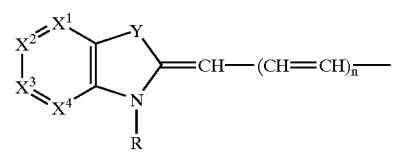

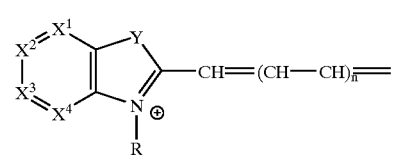

(e) each of B and C is $W^1$ if B and C are adjacent, and one of B and C is $W^1$ and one of B and C is $W^2$ if B and C are separated by one of A, D, E, and F;
(f) each of A, D, E, and f, unless absent according to (b), is selected from the group consisting of O, S, Se, Te, N—$R^c$, N($R^d$)($R^e$), and C($R^f$)($R^g$), wherein each of $R^c$, $R^d$, and $R^e$ is selected from the group consisting of aliphatic, heteroatom-substituted aliphatic, polyether, aromatic, reactive aliphatic, and reactive aromatic groups, $R^f$ and $R^g$ being selected from the group consisting of carboxylic acid, cyano, carboxamide, carboxylic ester, and aliphatic amine groups;
(g) n is independently selected for each of B and C from the group consisting of 0, 1, and 2;
(h) Y is independently selected for each of B and C from the group consisting of O, S, Se, Te, N—$R^h$, and C($R^i$)($R^j$), wherein $R^h$ is selected from the group consisting of H, aliphatic groups, alicyclic groups, aromatic groups, and reactive aliphatic groups, and wherein each of $R^i$ and $R^j$ is selected from the group consisting of aliphatic and reactive aliphatic groups;
(i) R is independently selected for each of B and C from the group consisting of H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound, provided that R in at least one of B and C is —(CH$_2$)$_P$—COOR$^k$, wherein P is an integer of at least 1, and R$^k$ is H or NHS;

(j) each of X$^1$, X$^2$, X$^3$, and X$^4$ is independently selected for each of B and C from the group consisting of N, O, S, and C—R$^l$, wherein R$^l$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and (k) each H may be independently replaced by a fluorine.

13. The composition of paragraph 12, wherein P is 5.

14. The composition of paragraph 12, wherein R in one of B and C is CH$_3$ or H.

15. The composition of paragraph 12, wherein the compound is symmetrical around Z.

16. The composition of paragraph 12, wherein the compound is asymmetric around Z.

17. The composition of paragraph 12, wherein R in each of B and C is —(CH$_2$)$_P$—COOR$^k$, wherein P is an integer of at least 1, and R$^k$ is H or NHS.

18. The composition of paragraph 12, wherein at least one of A, D, E, and F, unless absent according to (b), is S.

19. The composition of paragraph 12, wherein Z is based on squaric acid, croconic acid or rhodizonic acid.

20. The composition of paragraph 19, wherein Z is based on squaric acid.

21. A composition of matter comprising a photoluminescent compound, the photoluminescent compound comprising:

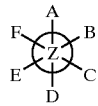

wherein:

(a) Z is a four, five, or six-member aromatic ring;

(b) A, B, C, D, E, and F are substituents of Z, wherein F is absent when Z is a five-member ring, and wherein E and F are absent when Z is a four-member ring;

(c) A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

(d) each of B and C is selected from the group consisting of W$^1$ and W$^2$, wherein W$^1$ and W$^2$ are given by

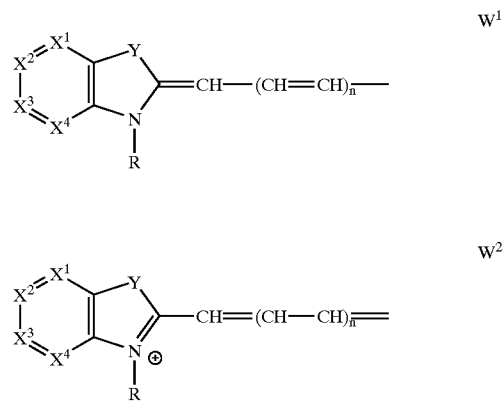

(e) each of B and C is W$^1$ if B and C are adjacent, and one of B and C is W$^1$ and one of B and C is W$^2$ if B and C are separated by one of A, D, E, and F;

(f) each of A, D, E, and F, unless absent according to (b), is selected from the group consisting of O, S, Se, Te, N—R$^c$, N(R$^d$)(R$^e$), and C(R$^f$)(R$^g$), wherein each of R$^c$, R$^d$, and R$^e$ is selected from the group consisting of aliphatic, heteroatom-substituted aliphatic, polyether, aromatic, reactive aliphatic, and reactive aromatic groups, R$^f$ and R$^g$ being selected from the group consisting of carboxylic acid, cyano, carboxamide, carboxylic ester, and aliphatic amine groups;

(g) n is independently selected for each of B and C from the group consisting of 0, 1, and 2;

(h) Y is independently selected for each of B and C from the group consisting of O, S, Se, Te, N—R$^h$, and C(R$^i$)(R$^j$), wherein R$^h$ is selected from the group consisting of H, aliphatic groups, alicyclic groups, aromatic groups, and reactive aliphatic groups, and wherein each of R$^i$ and R$^j$ is selected from the group consisting of aliphatic and reactive aliphatic groups;

(i) R is independently selected for each of B and C from the group consisting of H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;

(j) each of X$^1$, X$^2$, X$^3$, and X$^4$ is independently selected for each of B and C from the group consisting of N, O, S, and C—R$^k$, wherein R$^k$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring, provided that at least one of X$^1$, X$^2$, X$^3$, and X$^4$ is a heteroatom; and (k) each H may be independently replaced by a fluorine.

Although the invention has been disclosed in preferred forms, the specific embodiments thereof as disclosed and illustrated herein are not to be considered in a limiting sense, because numerous variations are possible. Applicant regards the subject matter of his invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A composition of matter comprising a photoluminescent compound, the photoluminescent compound having a four-, five-, or six-member aromatic ring Z, with substituents A, B, C, D, E, and F, wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is selected from the group consisting of =S, =Se, =Te, and =C(R$^a$)(R$^b$), wherein each of R$^a$ and R$^b$ is selected from the group consisting of carboxylic acid, cyano, carboxamide, carboxylic ester, and aliphatic amine groups; when the A substituent is negatively charged, A is selected from the group consisting of —S$^-$, —Se$^-$, —Te$^-$, and —C(R$^a$)(R$^b$)$^-$;

each B and C substituent is selected from the group consisting of W$^1$ and W$^2$, wherein W$^1$ and W$^2$ have the respective formulae

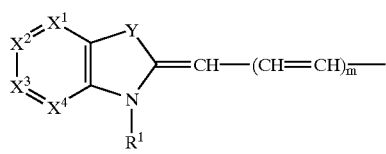

and

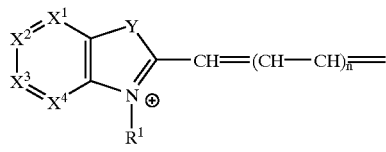

where each B and C substituent is W$^1$ if B and C are adjacent on Z, and one of B and C is W$^1$ and the other of B and C is W$^2$ if B and C are separated by one of A, D, E, and F on ring Z;

each D, E, and F substituent, when present and neutral, is independently selected from the group consisting of =O, =S, =Se, =Te, =N—R$^c$, —N(R$^d$)(R$^e$), and =C(R$^f$)(R$^g$), wherein each of R$^c$, R$^d$, and R$^e$ is selected from the group consisting of aliphatic, heteroatom-substituted aliphatic, polyether, aromatic, reactive aliphatic, and reactive aromatic groups, R$^f$ and R$^g$ being selected from the group consisting of carboxylic acid, cyano, carboxamide, carboxylic ester, and aliphatic amine groups; D, E, and F, when present and negatively charged, are independently selected from the group consisting of —O$^-$, —S$^-$, —Se$^-$, —Te$^-$, —(N—R$^c$)$^-$, and —(C(R$^f$)(R$^g$))$^-$;

m and n are independently selected from the group consisting of 0, 1, and 2;

Y is independently selected for each of B and C from the group consisting of O, S, Se, Te, N—R$^h$, and C(R$^i$)(R$^j$), wherein R$^h$ is selected from the group consisting of H, aliphatic groups, alicyclic groups, aromatic groups, and reactive aliphatic groups, and wherein each of R$^i$ and R$^j$ is selected from the group consisting of aliphatic and reactive aliphatic groups;

each R$^1$ is independently selected for each of B and C from the group consisting of H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;

each of X$^1$, X$^2$, X$^3$, and X$^4$ is independently selected for each of B and C from the group consisting of N, O, S, and C—R$^k$, wherein R$^k$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

2. The composition of claim 1, wherein the photoluminescent compound has a formula selected from the group consisting of

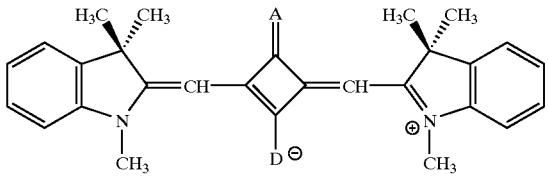

wherein A is =S or =C(R$^a$)(R$^b$), and D is —S or —C(R$^a$)(R$^b$);

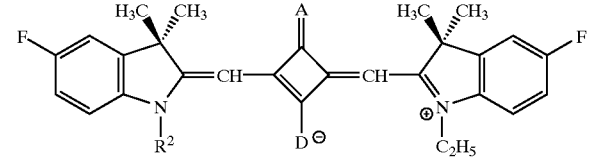

wherein A is =S, or =C(R$^a$)(R$^b$);

D is —O or —S; and

R² is H, —(CH₂)ₖ—L, or —(CF₂)ₖ—L where k=1–30, and L is one of H, F, Cl, Br, I, CH₂—NH₂, SO₃⁻, COOH, and CO—NHS;

and

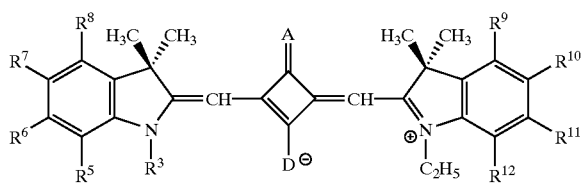

where A is =S, or =C(Rᵃ)(Rᵇ);

D is —O or —S; and

R³ is H, —(CH₂)ₖ—L, or —(CF₂)ₖ—L where k=1–30, and L is one of H, F, Cl, Br, I, CH₂—NH₂, SO₃⁻, COOH, and CO—NHS; and R⁵–R¹² are each independently H, F, or SO₃⁻.

3. The composition of claim 1, wherein Z is based on squaric acid, croconic acid, or rhodizonic acid.

4. The composition of claim 1, wherein D is selected from the group consisting of =S, =Se, =Te, —S⁻, —Se⁻, and —Te⁻.

5. The composition of claim 1, wherein at least one substituent of Z includes a reactive group.

6. The composition of claim 5, wherein the reactive group is selected for reacting with amine moieties from the group consisting of N-hydroxysuccinimide esters, isothiocyanates, and sulfonyl halides.

7. The composition of claim 5, wherein the reactive group is selected for reacting with thiol moieties from the group consisting of iodoacetamides and maleimides.

8. The composition of claim 5, wherein the reactive group is selected for reacting with nucleic acids from the group consisting of phosphoramidites.

9. The composition of claim 1, wherein at least one substituent of Z includes a linked carrier.

10. The composition of claim 9, wherein the carrier is selected from the group consisting of polypeptides, polynucleotides, beads, microplate well surfaces, and other solid surfaces.

11. The composition of claim 10, wherein the carrier is a polypeptide or a polynucleotide.

12. The composition of claim 1, further comprising a carrier, which is associated noncovalently with the photoluminescent compound.

13. The composition of claim 1, further comprising a carrier, which is associated covalently with the photoluminescent compound through reaction with a reactive group on at least one substituent of Z.

14. The composition of claim 1, wherein at least one substituent of Z includes an ionic substituent capable of increasing the hydrophilicity of the entire photoluminescent compound.

15. The composition of claim 14, wherein the ionic substituent is selected from the group consisting of SO₃⁻, COO⁻, and N(R¹)₃⁺, wherein R¹ is an aliphatic or aromatic moiety.

16. The composition of claim 1, wherein the substituents of Z are selected so that the photoluminescent compound is electrically, neutral, increasing its hydrophobicity.

17. The composition of claim 1, wherein Rᵃ is (CH₂)ₙCOOH or (CH₂)ₙNH₂.

18. The composition of claim 1, wherein the photoluminescent compound is suitable for excitation in the red or near infrared region.

19. The composition of claim 1, wherein the photoluminescent compound is capable of emitting light having a wavelength in the range 600–900 nanometers.

20. The composition of claim 1, wherein the photoluminescent compound has a Stokes' shift of at least about 5 nanometers.

21. The composition of claim 1, wherein the photoluminescent compound is capable of covalently reacting with at least one of the following: biological cells, DNA, lipids, nucleotides, polymers, proteins, and pharmacological agents.

22. The composition of claim 1, wherein the photoluminescent compound is covalently or noncovalently attached to at least one of the following: biological cells, DNA, lipids, nucleotides, polymers, proteins, and pharmacological agents.

23. The composition of claim 1, wherein the photoluminescent compound is symmetric about Z.

24. The composition of claim 1, wherein the photoluminescent compound is asymmetric about Z.

25. The composition of claim 1, wherein m and n are 1.

26. The composition of claim 1, wherein B and C are adjacent, linked to Z through a 1,2 linkage.

27. The composition of claim 1, wherein B and C are separated by one of A, D, E, or F, linked to Z through a 1,3 linkage.

28. The composition of claim 1, further comprising a second compound selected from the group consisting of luminophores and chromophores.

29. The composition of claim 28, wherein one of the photoluminescent compound and the second compound is an energy transfer donor and the other is an energy transfer acceptor.

30. The composition of claim 1, wherein the photoluminescent compound may be induced to luminesce by exposing the photoluminescent compound to one or more of the following: electromagnetic energy, chemical energy, and electrochemical energy.

31. A photoluminescent compound having the formula

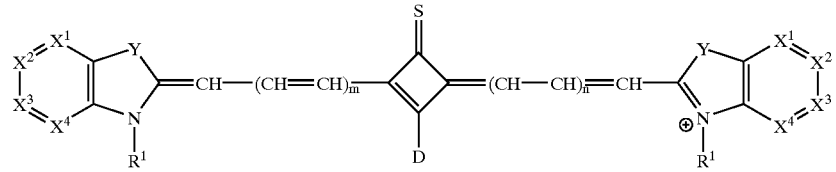

wherein D is selected from the group consisting of O⁻, S⁻, Se⁻, Te⁻, N—(Rᶜ)⁻, N(Rᵈ)(Rᵉ), and C(Rᶠ)(Rᵍ)⁻, wherein each of Rᶜ, Rᵈ, and Rᵉ is selected from the group consisting of aliphatic, heteroatom-substituted aliphatic, polyether, aromatic, reactive aliphatic, and reactive aromatic groups, Rᶠ and Rᵍ being selected from the group consisting of carboxylic acid, cyano, carboxamide, carboxylic ester, and aliphatic amine groups;

m and n are independently selected from the group consisting of 0, 1, and 2;

Y is independently selected for each of B and C from the group consisting of O, S, Se, Te, N—$R^h$, and $C(R^i)(R^j)$, wherein $R^h$ is selected from the group consisting of H, aliphatic groups, alicyclic groups aromatic groups, and reactive aliphatic groups, and wherein each of $R^i$ and $R^j$ is selected from the group consisting of aliphatic and reactive aliphatic groups;

each $R^1$ is independently selected for each of B and C from the group consisting of H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of H, N, O, S, and C—$R^k$, wherein $R^k$ is selected from the group consisting of H, F, Cl, Br, I, aliphatic groups, alicyclic groups, aromatic groups, linked carriers reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

32. A photoluminescent compound having the formula

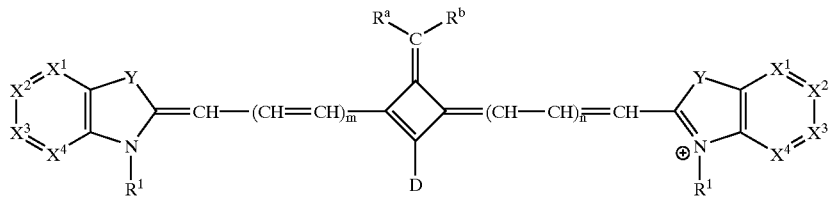

wherein each of $R^a$ and $R^b$ is selected from the group consisting of carboxylic acid, cyano, carboxamide, carboxylic ester, and aliphatic amine groups;

D is selected from the group consisting of $O^-$, $S^-$, $Se^-$, $Te^-$, N—$(R^c)^-$, $N(R^d)(R^e)$, and $C(R^f)(R^g)^-$, wherein

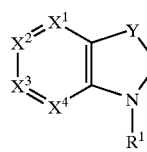

each of $R^c$, $R^d$, and $R^e$ is selected from the group consisting of aliphatic, heteroatom-substituted aliphatic, polyether, aromatic, reactive aliphatic, and reactive aromatic groups, $R^f$ and $R^g$ being selected from the group consisting of carboxylic acid, cyano, carboxamide, carboxylic ester, and aliphatic amine groups;

m and n are independently selected from the group consisting of 0, 1, and 2;

Y is independently selected for each of B and C from the group consisting of O, S, Se, Te, N—$R^h$, and $C(R^i)(R^j)$, wherein $R^h$ is selected from the group consisting of H, aliphatic groups, alicyclic groups, aromatic groups, and reactive aliphatic groups, and wherein each of $R^i$ and $R^j$ is selected from the group consisting of aliphatic and reactive aliphatic groups;

each $R^1$ is independently selected for each of B and C from the group consisting of H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of H, N, O, S, and C—$R^k$, wherein $R^k$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

33. A photoluminescent compound having the formula

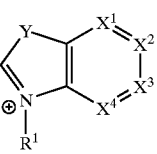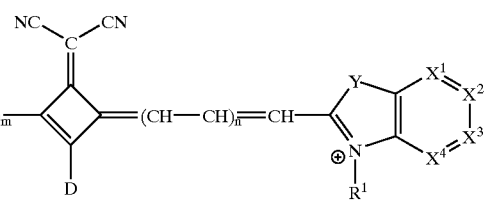

wherein D is selected from the group consisting of $O^-$, $S^-$, $Se^-$, $Te^-$, N—$(R^c)^-$, $N(R^d)(R^e)$, and $C(R^f)(R^g)^-$, wherein each of $R^c$, $R^d$, and $R^e$ is selected from the group consisting of aliphatic, heteroatom-substituted aliphatic, polyether, aromatic, reactive aliphatic, and reactive aromatic groups, $R^f$ and $R^g$ being selected from the group consisting of carboxylic acid, cyano, carboxamide, carboxylic ester, and aliphatic amine groups;

m and n are independently selected from the group consisting of 0, 1, and 2;

Y is independently selected for each of B and C from the group consisting of O, S, Se, Te, N—$R^h$, and C($R^i$)($R^j$), wherein $R^h$ is selected from the group consisting of H, aliphatic groups, alicyclic groups, aromatic groups, and reactive aliphatic groups, and wherein each of $R^i$ and $R^j$ is selected from the group consisting of aliphatic and reactive aliphatic groups;

each $R^1$ is independently selected for each of B and C from the group consisting of H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of H, N, O, S, and C—$R^k$, wherein $R^k$ is selected from the group consisting of H, F, Cl, Br, I, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

* * * * *

UNITED STATES PATENT AND TRADEMARK OFFICE
CERTIFICATE OF CORRECTION

PATENT NO.    : 6,538,129 B1                                                       Page 1 of 1
DATED         : March 25, 2003
INVENTOR(S)   : Ewald A. Terpetschnig, Leonid D. Patsenker and Berhard Oswald It is certified that error appears in the above-identified patent and that said Letters Patent is hereby corrected as shown below:

<u>Column 41,</u>
Line 9, after "alicyclic groups" insert -- , --.
Line 26, after "linked carriers" insert -- , --.

<u>Column 42,</u>
Line 20, after "capable" delete "-".

<u>Column 44,</u>
Line 14, after "heterocy" insert -- - --.

Signed and Sealed this

Thirtieth Day of September, 2003

JAMES E. ROGAN
*Director of the United States Patent and Trademark Office*